(12) United States Patent
Peterson et al.

(10) Patent No.: US 7,446,231 B2
(45) Date of Patent: Nov. 4, 2008

(54) STABILIZATION OF A HYDROFORMYLATION PROCESS

(75) Inventors: Ronald R Peterson, St. Albans, WV (US); Thomas C. Eisenschmid, Cross Lanes, WV (US); David R. Bryant, Charleston, WV (US); Morteza Mokhtarzadeh, Charleston, WV (US)

(73) Assignee: Union Carbide Chemicals & Plastics Technology Corporation, Midland, MI (US)

( * ) Notice: Subject to any disclaimer, the term of this patent is extended or adjusted under 35 U.S.C. 154(b) by 0 days.

(21) Appl. No.: 11/658,192

(22) PCT Filed: Jul. 19, 2005

(86) PCT No.: PCT/US2005/025571

§ 371 (c)(1), (2), (4) Date: Jan. 22, 2007

(87) PCT Pub. No.: WO2006/020287

PCT Pub. Date: Feb. 23, 2006

(65) Prior Publication Data

US 2008/0027248 A1 Jan. 31, 2008

Related U.S. Application Data

(60) Provisional application No. 60/598,032, filed on Aug. 2, 2004.

(51) Int. Cl.
C07C 45/50 (2006.01)

(52) U.S. Cl. ........................... 568/451; 568/454

(58) Field of Classification Search ................ 568/451, 568/454
See application file for complete search history.

(56) References Cited

U.S. PATENT DOCUMENTS

| | | |
|---|---|---|
| 3,527,809 A | 9/1970 | Pruett et al. |
| 4,148,830 A | 4/1979 | Pruett et al. |
| 4,247,486 A | 1/1981 | Brewester et al. |
| 4,518,809 A | 5/1985 | Forster et al. |
| 4,528,403 A | 7/1985 | Tano et al. |
| 4,593,127 A | 6/1986 | Bunning et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,885,401 A | 12/1989 | Billig et al. |
| 5,095,710 A | 3/1992 | Black et al. |
| 5,102,505 A | 4/1992 | Sorensen |
| 5,110,990 A | 5/1992 | Blessing et al. |
| 5,113,022 A | 5/1992 | Abatjoglou et al. |
| 5,114,473 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,288,918 A | 2/1994 | Maher et al. |
| 5,312,996 A | 5/1994 | Packett |
| 5,360,938 A | 11/1994 | Babin et al. |
| 5,364,950 A | 11/1994 | Babin et al. |
| 5,391,801 A | 2/1995 | Sato et al. |
| 5,449,653 A | 9/1995 | Briggs et al. |
| 5,491,266 A | 2/1996 | Babin et al. |
| 5,763,679 A | 6/1998 | Nicholson et al. |
| 5,874,639 A | 2/1999 | Nicholson et al. |
| 5,874,640 A | 2/1999 | Bryant et al. |
| 5,892,119 A | 4/1999 | Bryant et al. |
| 5,932,772 A | 8/1999 | Argyropoulos et al. |
| 5,952,530 A | 9/1999 | Argyropoulos et al. |
| 6,090,987 A | 7/2000 | Billig et al. |
| 6,294,700 B1 | 9/2001 | Kanel et al. |
| 6,303,829 B1 | 10/2001 | Kanel et al. |
| 6,303,830 B1 | 10/2001 | Argyropoulos et al. |
| 6,307,109 B1 | 10/2001 | Kanel et al. |
| 6,307,110 B1 | 10/2001 | Argyropoulos et al. |

FOREIGN PATENT DOCUMENTS

| | | |
|---|---|---|
| EP | 0589463 B1 | 8/1997 |
| SU | 1527234 A1 | 12/1989 |
| SU | 1555323 | 4/1990 |
| WO | WO 2005/007602 | 1/2005 |

OTHER PUBLICATIONS

Co-Pending U.S. Appl. No. 10/562,602, filed Dec. 28, 2005; "Minimization of Ligand Degradation Products, or Reversion or Same to Useful Ligands," John R. Briggs, et al.; corresponding to International Patent Application publication WO 2005/007602, Jan. 27, 2005.

*Primary Examiner*—Sikarl A Witherspoon

(57) ABSTRACT

An improved hydroformylation process involving reacting one or more reactants, such as an olefin, with carbon monoxide and hydrogen in the presence of a hydroformylation catalyst, to produce a reaction product fluid comprising one or more products, preferably aldehydes; wherein said process is conducted in a region of the hydroformylation rate curve that is negative or inverse order in carbon monoxide, which is sufficient to prevent and/or lessen deactivation of the hydroformylation catalyst; and wherein total pressure is controlled at a predetermined target value and/or vent flow rate is controlled at a predetermined target value, by adjusting a flow of a carbon-monoxide containing inlet gas, so as to prevent and/or lessen cycling of process parameters, e.g., reaction rate, total pressure, vent flow rate, and/or temperature.

28 Claims, 20 Drawing Sheets

1. Positive order region
2. Negative or inverse order region

1. Minimum base synthesis gas feed flow rate
2. Maximum base synthesis gas feed flow rate
3. Target total reactor pressure 1. Impeller
2. Impeller shaft
3. Propylene feed line and feed flow control
4. Syngas feed line, sparger and feed flow controller
5. Vent flow line and vent flow control
6. Total pressure sensor
7. Exit line for product solution/catalyst to product recovery system
8. Feed line for catalyst returned from product recovery system 1. Impeller
2. Impeller shaft
3. Propylene feed line and feed flow control
4. Syngas feed line, sparger and feed flow controller
5. Vent flow line and vent flow control
6. Total pressure sensor
7. Exit line for product solution/catalyst to product recovery system
8. Feed line for catalyst returned from product recovery system
9. Reactor total pressure control 1. Impeller
2. Impeller shaft
3. Propylene feed line and feed flow control
4. Syngas feed line, sparger and feed flow controller
6. Total pressure sensor
7. Exit line for product solution/catalyst to product recovery system
8. Feed line for catalyst returned from product recovery system
10. Reactor total pressure control
11. Reactor vent flow sensor

FIG 13

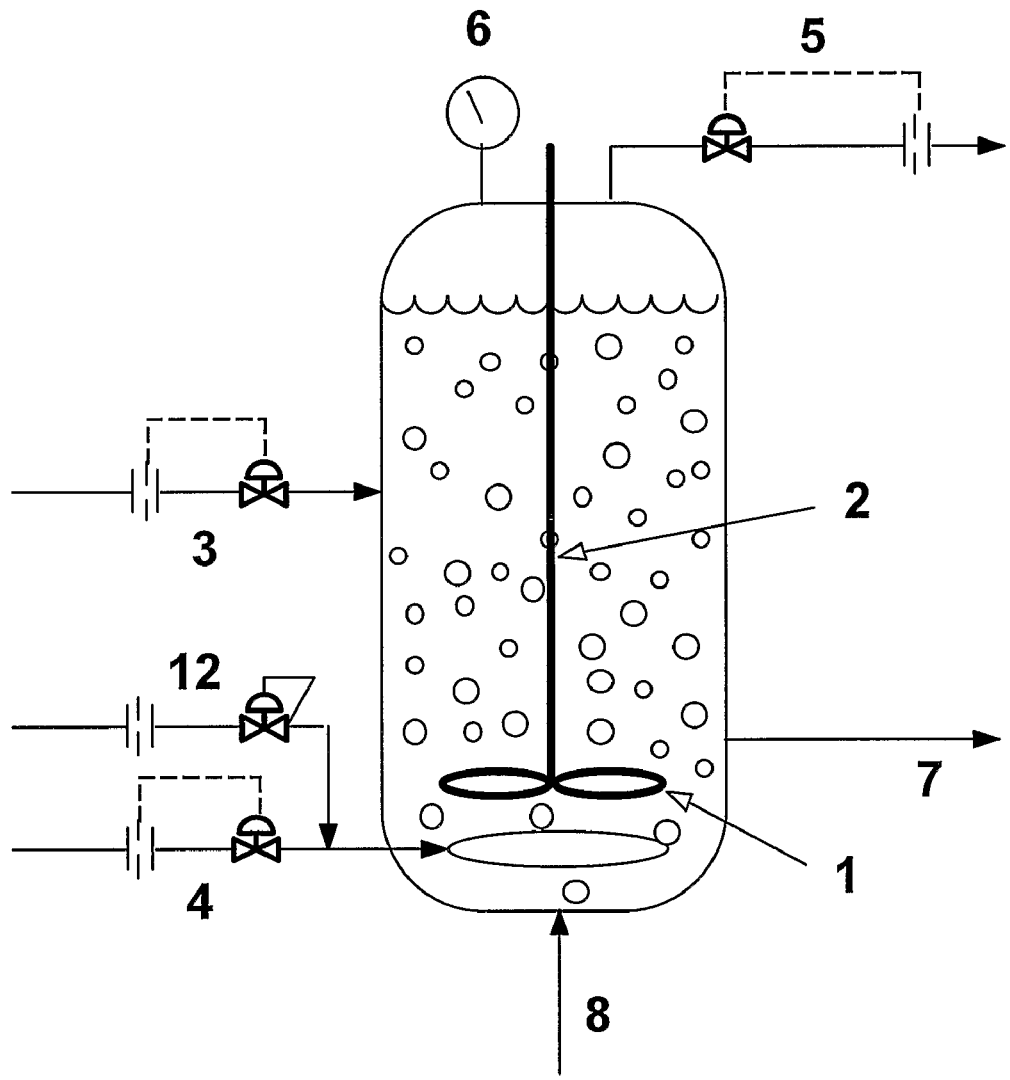

1. Impeller
2. Impeller shaft
3. Propylene feed line and feed flow control
4. Syngas feed line, sparger and feed flow controller
5. Vent flow line and vent flow control
6. Total pressure sensor
7. Exit line for product solution/catalyst to product recovery system
8. Feed line for catalyst returned from product recovery system
12. Carbon monoxide feed controller for total reactor pressure control

FIG 16

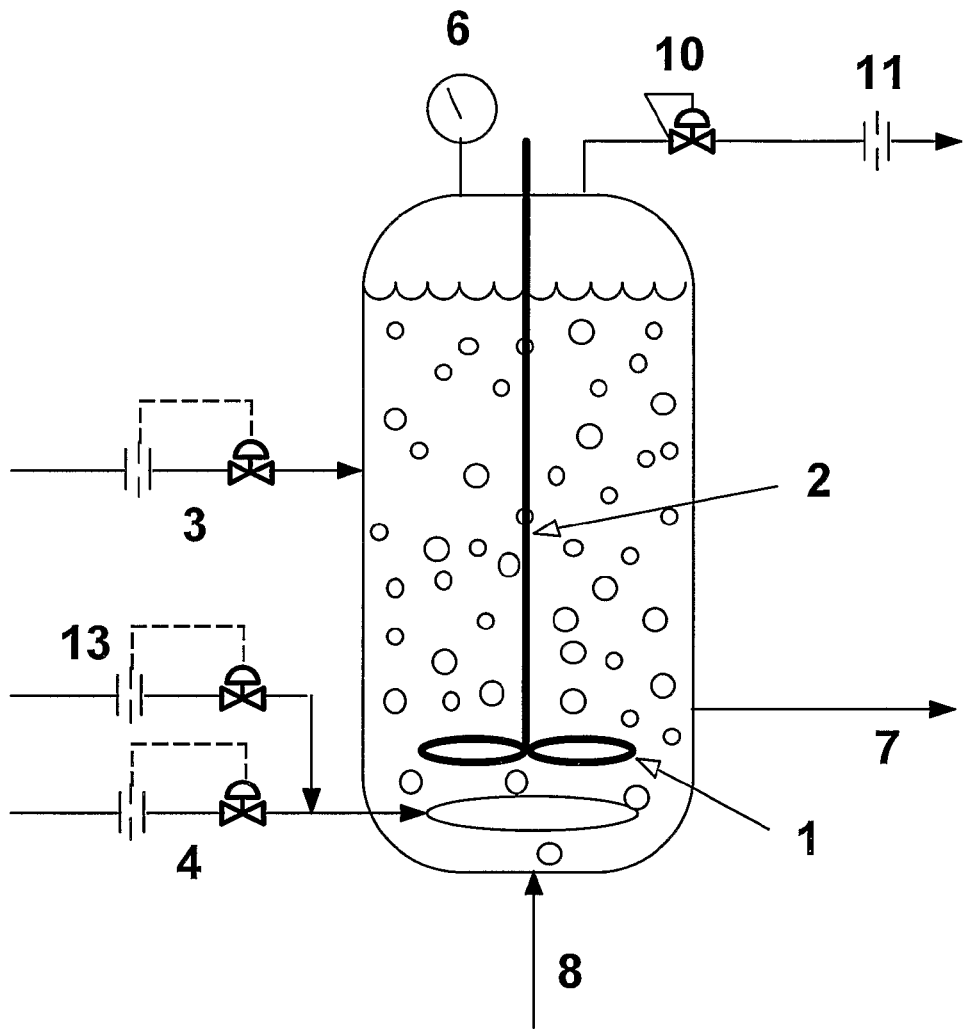

1. Impeller
2. Impeller shaft
3. Propylene feed line and feed flow control
4. Syngas feed line, sparger and feed flow controller
6. Total pressure sensor
7. Exit line for product solution/catalyst to product recovery system
8. Feed line for catalyst returned from product recovery system
10. Reactor total pressure control
11. Reactor vent flow sensor
13. Carbon monoxide feed flow controller

FIG 19

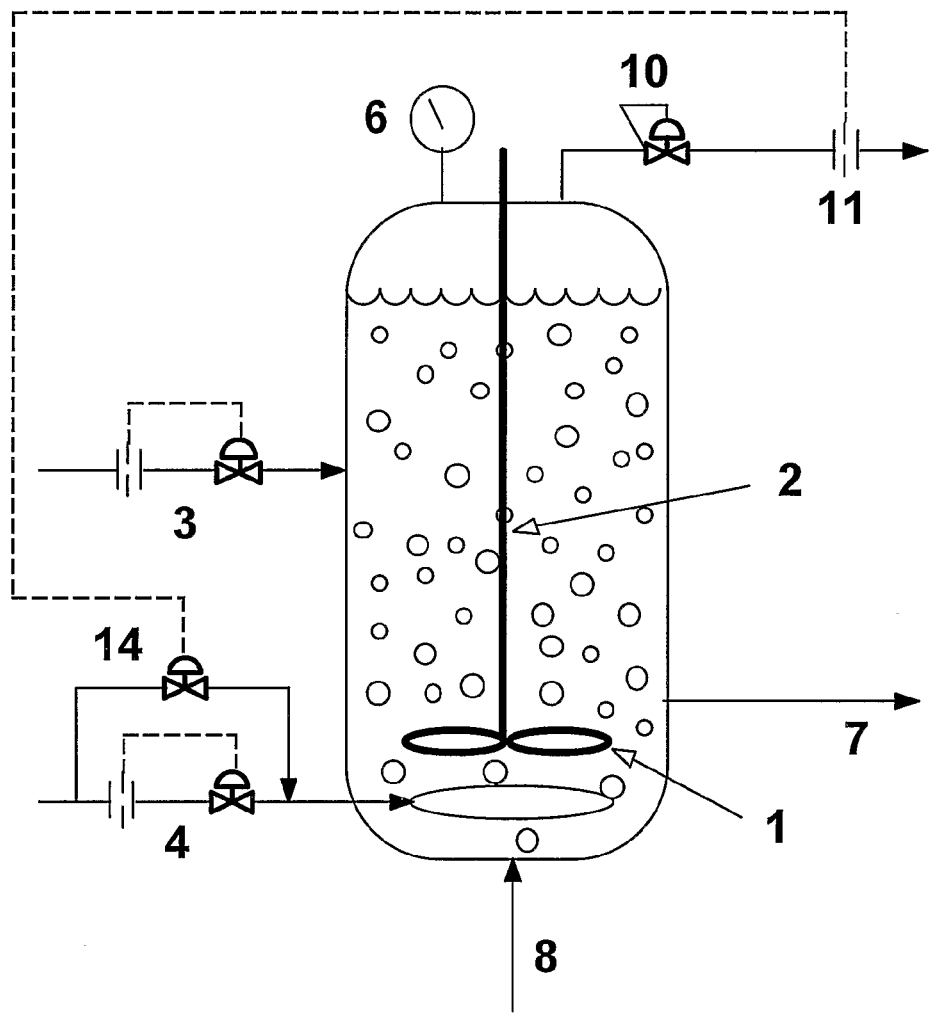

1. Impeller
2. Impeller shaft
3. Propylene feed line and feed flow control
4. Syngas feed line, sparger and feed flow controller
6. Total pressure sensor
7. Exit line for product solution/catalyst to product recovery system
8. Feed line for catalyst returned from product recovery system
10. Reactor total pressure control
11. Reactor vent flow sensor
14. Syngas feed line to control total reactor vent flow rate 1. Positive order region
2. Negative or inverse order region

STABILIZATION OF A HYDROFORMYLATION PROCESS

This application is a 371 filing of International Patent Application No. PCT/US2005/025571, filed Jul. 19, 2005, which claims the benefit of U.S. Provisional Patent Application Ser. No. 60/598,032, filed Aug.2, 2004.

BACKGROUND OF THE INVENTION

This invention pertains to a method of stabilizing a hydroformylation process against rapid, often extreme, change or cycling of reaction rate and/or process parameters, such as total pressure, vent flow rate, and temperature.

It is well known in the art that aldehydes may be readily produced by reacting an olefinically unsaturated compound with carbon monoxide and hydrogen in the presence of a metal-organophosphorus ligand complex catalyst, and that preferred processes involve continuous hydroformylation and recycling of a solution containing a Group VIII-organopolyphosphite ligand complex catalyst. Rhodium is a preferred Group VIII metal. Such art is exemplified in U.S. Pat. No. 4,148,830; U.S. Pat. No. 4,717,775; and U.S. Pat. No. 4,769,498 . Aldehydes produced by such processes have a wide range of utility, for example, as intermediates for hydrogenation to aliphatic alcohols, for amination to aliphatic amines, for oxidation to aliphatic acids, and for aldol condensation to produce plasticizers.

The art recognizes that normal or unbranched aldehydes generally provide more value than their iso- or branched isomers. Additionally, it is known that the normal to branched isomer ratio is a function of carbon monoxide partial pressure, and typically lower carbon monoxide partial pressures give products with higher normal to branched ratios. Rhodium-organopolyphosphite ligand complex catalyzed processes have been shown to give very desirable normal to branched isomer ratios.

Notwithstanding the benefits attendant with such metal-organophosphorus ligand complex catalyzed hydroformylation processes, stabilization of the catalyst and particularly the organopolyphosphite ligand remains a primary concern. Loss of catalyst or catalytic activity due to undesirable side-reactions of the expensive rhodium catalysts can be detrimental to the production of the desired aldehyde. Likewise, degradation of the organophosphorus ligand during the hydroformylation process can produce poisoning compounds (for example, poisoning organomonophosphites), or inhibitors, or acidic phosphorus byproducts that can lower the catalytic activity of the rhodium catalyst. Production costs of the aldehyde product increase when the productivity of the catalyst decreases.

In hydroformylation processes a major cause of organopolyphosphite ligand degradation and rhodium-organopolyphosphite ligand complex catalyst deactivation derives from the hydrolytic instability of the organopolyphosphite ligand. All organopolyphosphites are susceptible to hydrolysis to some degree or another, the rate of hydrolysis generally being dependent on the stereochemical nature of the organopolyphosphite. In general, the bulkier the steric environment around the phosphorus atom, the slower may be the hydrolysis rate. All such hydrolysis reactions, however, invariably produce acidic phosphorus compounds that further catalyze the hydrolysis reactions. The hydrolysis of a tertiary organophosphite, for example, produces a phosphonic acid diester, which in turn is hydrolysable to phosphoric acid. Other hydrolysis side-reactions produce strong aldehyde acids.

Indeed, even highly desirable sterically-hindered organobisphosphite ligands, which tend to be less hydrolysable, can react with aldehyde products to form poisoning organomonophosphites, which are not only catalytic inhibitors, but far more susceptible to hydrolysis and the formation of aldehyde acid byproducts, for example, hydroxyl alkyl phosphonic acids, as shown in U.S. Pat. No. 5,288,918 and U.S. Pat. No. 5,364,950. The hydrolysis of organopolyphosphite ligands may be considered as being autocatalytic, and if left unchecked, the catalyst system of a continuous liquid recycle hydroformylation process will become increasingly acidic in time, with the organomonophosphites and/or acidic phosphorus byproducts binding the catalytic metal in the form of inhibiting complexes. As a consequence, the activity of the metal-organopolyphosphite ligand complex catalyst declines as inhibiting complex concentration increases. Thus, the eventual build-up of unacceptable amounts of such poisoning and inhibiting materials causes the destruction of the organopolyphosphite ligand, thereby rendering the hydroformylation catalyst ineffective (deactivated) and the valuable rhodium metal susceptible to loss; such as, by precipitation and/or depositing on the walls of the reactor.

The art discloses, as shown in U.S. Pat. No. 5,763,679, that deactivation of metal-organophosphorus ligand complex catalysts caused by inhibiting or poisoning phosphorus compounds can be reversed or reduced by conducting the hydroformylation process in a reaction region where the hydroformylation reaction rate is of a negative or inverse order in carbon monoxide. As used herein, a hydroformylation reaction rate that is negative or inverse order in carbon monoxide refers to a hydroformylation region wherein the hydroformylation reaction rate increases as carbon monoxide partial pressure decreases, and wherein the hydroformylation reaction rate decreases as carbon monoxide partial pressure increases. In contrast, a hydroformylation process that is positive order in carbon monoxide occurs when the hydroformylation reaction rate increases as the carbon monoxide partial pressure increases, and when the hydroformylation reaction rate decreases as the carbon monoxide partial pressure decreases. (Positive and inverse order regions of the rate curve are illustrated hereinafter.) At higher carbon monoxide partial pressure, in the negative or inverse order region of the rate curve, carbon monoxide coordinates more effectively with and competes more effectively for the metal of the metal-organophosphorus ligand complex catalyst, as compared with the inhibiting or poisoning phosphorus compounds. Thus, the concentration of free inhibiting or poisoning phosphorus compounds in the hydroformylation reaction fluid is increased, such that the inhibiting or poisoning phosphorus compounds can be readily hydrolyzed with water and/or weakly acidic compounds. The resulting hydrolysis fragments can be beneficially scrubbed from the reaction fluid.

Higher carbon monoxide partial pressures in the negative or inverse order region of the rate curve provide additional desirable benefits in that olefin efficiency losses due to hydrogenation can be reduced. Higher carbon monoxide partial pressures give both higher catalytic activity and lower efficiency losses to alkanes. Moreover, undesirable olefin isomerizations may also be reduced.

Operating near the peak of the hydroformylation reaction rate curve in the inverse carbon monoxide partial pressure region can have additional desirable benefits in that the normal/branched isomer product ratio can be increased while also increasing the catalyst productivity and/or hydroformylation reaction rate.

Nevertheless, operation of the hydroformylation process in the negative or inverse order region of the rate curve with respect to carbon monoxide presents problems, which are not typically seen on the positive order side of the rate curve. More specifically, when the hydroformylation process is positive order in carbon monoxide, an increase in reaction rate consumes carbon monoxide, which leads consequentially to a decrease in carbon monoxide partial pressure. The decrease in carbon monoxide partial pressure (or concentration) slows the reaction rate such that the reaction temperature, carbon monoxide partial pressure, hydrogen partial pressure, and total pressure can be controlled. Accordingly, when the process is operated under positive order in carbon monoxide, the process can be readily controlled; but as noted hereinbefore a steadily declining catalyst activity is observed due to an accumulation of inhibiting and poisoning phosphorus byproducts and metal-ligand complexes thereof. In contrast, when the process is negative order in carbon monoxide, an increase in reaction rate consumes carbon monoxide; but the resulting lower partial pressure of carbon monoxide further increases the hydroformylation reaction rate. Moreover, the increase in reaction rate will be further enhanced as a result of the heat of reaction, because hydroformylations are exothermic. In a batch process, a feedback loop develops that can result in essentially rapid and complete consumption of the limiting reactant and termination of the hydroformylation process. During continuous operation under negative order conditions, the hydroformylation reaction rate tends to cycle, as does the total pressure, vent flow, and/or temperature. As used herein, "cycling" refers to periodic and often extreme changes in process parameters (for example, reaction rate, partial and/or total pressures, vent flow, and/or temperature). Cycling disadvantageously disrupts steady operation. Thus, when operating in the negative order region of the rate curve, although the detrimental effects of inhibiting phosphorus byproducts can be reversed or reduced, the hydroformylation process itself becomes more difficult to stabilize and control. Moreover, operation under negative order conditions generally necessitates operation at high carbon monoxide partial pressures well away from the peak of the Hydroformylation Rate versus Carbon Monoxide Partial Pressure curve. Disadvantageously, operation further from the peak in the region that is negative order in carbon monoxide produces a lower normal to branched isomer ratio of the aldehyde product.

U.S. Pat. No. 5,763,679 discloses a method of controlling cycling and maintaining steady reaction rate and process parameters while operating under negative order in carbon monoxide. The disclosed method requires controlling the differential between a reaction product effluent temperature and a heat exchanger's coolant temperature to less than about 25° C. Disadvantageously, this prior art method requires large and costly heat exchangers. Also, due to the large thermal load of the reaction fluid, the time constant for recovery from a sudden temperature deviation may be unacceptably slow.

EP-B1-0589463 discloses a method of controlling the stability of hydroformylation processes by varying the flow rate of a synthesis feed gas or the flow rate of a vent gas to maintain a predetermined constant carbon monoxide partial pressure in the hydroformylation process. The reference is silent with regard to floating carbon monoxide partial pressure and to operating in the negative or inverse order region of the hydroformylation rate curve with respect to carbon monoxide. Disadvantageously, the disclosed process is not suitably adapted for hydroformylation processes that employ hydrolysable organophosphorus ligands and therefore prefer operation in the negative or inverse order region of the rate curve.

SU-A1-1527234 discloses a method of controlling the stability of hydroformylation processes by varying the flow rate of the olefinic reactant at constant vent flow, while operating the hydroformylation process in the positive region of the rate curve with respect to the olefin. Disadvantageously, the disclosed process is not suitably adapted to hydroformylation processes that employ hydrolysable organophosphorus ligands and therefore prefer operation in the negative or inverse order region of the rate curve.

In view of the above, it would be desirable to discover an improved hydroformylation process that readily controls sudden changes and/or cycling of process parameters and provides for process stability while operating under conditions wherein the hydroformylation reaction rate is negative or inverse order in carbon monoxide. Desirably, such an improved process should eliminate the need for large and costly heat exchangers and should provide for a quick response to deviations from process control. Desirably, such an improved process should also enhance catalyst lifetime by minimizing the detrimental effects of inhibiting or poisoning phosphorus byproducts. Moreover, such an improved process should desirably provide for a high normal to branched product isomer ratio while simultaneously providing for higher catalyst productivity and/or hydroformylation reaction rate, acceptable catalyst lifetime, acceptable reactor stability, and minimal cycling problems. A process possessing all of the aforementioned properties should find increased commercial appeal.

SUMMARY OF THE INVENTION

The invention described herein provides for a novel and improved hydroformylation process comprising reacting one or more reactants, carbon monoxide, and hydrogen in the presence of a hydroformylation catalyst to produce a reaction product fluid comprising one or more products, wherein said process is conducted at a carbon monoxide partial pressure such that reaction rate increases as carbon monoxide partial pressure decreases and the reaction rate decreases as carbon monoxide partial pressure increases; and wherein the following process steps are conducted to stabilize reaction rate, total pressure, vent flow rate, reaction temperature or a combination thereof, the process steps comprising at least one of the following process control schemes selected from:

Scheme A:

(a1) establishing a target total pressure;

(a2) detecting the total pressure, and determining the difference between the detected total pressure and the target total pressure; and (a3) based on the pressure difference measured in step (a2), manipulating a feed flow of gas comprising carbon monoxide to adjust the detected total pressure essentially to the target total pressure; and Scheme B:

(b1) establishing a target vent flow rate;

(b2) detecting the vent flow rate, and determining the difference between the detected vent flow rate and the target flow rate; and (b3) based on the vent flow rate difference measured in step (b2), manipulating a feed flow rate of gas comprising carbon monoxide to adjust the detected vent flow rate essentially to the target vent flow rate.

In another aspect of this invention, process steps (a1) through (a3) and process steps (b1) through (b3) are all implemented so as to adjust the detected total pressure essentially to the target total pressure and to adjust the detected vent flow rate essentially to the target vent flow rate.

The term "total pressure" shall refer to the total gas pressure of the process. The term "manipulating" shall mean any or all of the following words including "varying," "adjusting," "adapting," or "changing."

The novel hydroformylation process invention described hereinabove effectively controls sudden changes and/or cycling of process parameters and provides for process stability while operating under conditions wherein the hydroformylation reaction rate is negative or inverse order in carbon monoxide, such that reaction rate decreases as carbon monoxide partial pressure increases and reaction rate increases as carbon monoxide partial pressure decreases. In a novel aspect and in contrast to the prior art, this invention allows for fluctuation or floating of the carbon monoxide partial pressure up and down, such that reaction rate can be quenched or accelerated, as desired, to stabilize reaction rate and process parameters. Beneficially, the process of this invention achieves this reaction stability and prevents and/or lessens cycling of process parameters in a simple and cost effective fashion by eliminating the need for large and costly heat exchangers employed in the prior art. Moreover, as compared with the prior art, the process of this invention advantageously provides for improved and more rapid recovery from sudden and extreme process deviations. With stable operation in the negative or inverse order region of the rate curve, catalyst lifetime is beneficially enhanced by minimizing the detrimental effects of poisoning or inhibiting phosphorus ligand byproducts. As a further advantage, the process of this invention allows for operation in the inverse order region at carbon monoxide partial pressures nearer to the peak of the Hydroformylation Rate versus Carbon Monoxide Partial Pressure curve (illustrated hereinafter), which beneficially provides for higher hydroformylation reaction rates and/or catalyst productivity and higher normal to branched product ratios. No need exists to overfeed carbon monoxide to the process, which is kinetically controlled. Kinetic control, which leads to higher reaction rates, is more preferable than present-day mass transfer methods of process control. Advantageously, the process of this invention also provides for reduced alkane formation and reduced olefin isomerization, both features increasing the efficient use of olefin reactant. Finally, the process of this invention provides a method for determining, for any selected organopolyphosphite ligand, the optimal range of carbon monoxide partial pressures within the inverse order region of the rate curve and provides a method for stable operation within this range.

In another aspect, this invention is a novel apparatus for stabilizing a hydroformylation process comprising:

a reactor comprising a means for feeding one or more reactants; a means for feeding a synthesis gas; optionally, a means for feeding a secondary source of carbon monoxide; a means for feeding a catalyst solution; a means for venting reaction and inert gases; a means for withdrawing a reaction fluid; a means for measuring total gas pressure; and a means for measuring vent flow rate of reaction and inert gases; and wherein the apparatus further comprises at least one of the following design schemes selected from:

Design A:
(a1) a means for determining a pressure differential between a target total gas pressure and the measured total gas pressure;
(a2) a means for generating a signal corresponding to the pressure differential;
(a3) a means for receiving the signal from (a2) and for determining and sending an output signal to manipulate the flow rate of synthesis gas and/or secondary source of carbon monoxide to adjust the measured total pressure to the target total pressure; and Design B:
(b1) a means for determining a vent flow rate differential between a target vent flow rate and the measured vent flow rate;
(b2) a means for generating a signal corresponding to the vent flow rate differential;
(b3) a means for receiving the signal from (b2) and for determining and sending an output signal to manipulate the flow rate of synthesis gas and/or secondary source of carbon monoxide to adjust the measured vent flow rate to the target vent flow rate.

In an alternative embodiment, the apparatus may comprise all of design features (a1) through (a3) and (b1) through (b3).

DRAWINGS

FIG. 13 illustrates a continuous hydroformylation reactor with olefin and syngas feed flow controls, vent flow control, and control of total pressure in accordance with the invention through a secondary carbon monoxide feed line.

FIG. 16 illustrates a continuous hydroformylation reactor with olefin, carbon monoxide, and syngas feed flow controls, and for comparative purposes versus the reactor of FIG. 13, total pressure control through a vent line sensor and pressure control valve.

FIG. 19 illustrates a continuous hydroformylation reactor with olefin and syngas feed flow controls, and in accordance with the invention, total control of pressure through a back pressure regulator in the vent line and secondary syngas feed flow control to control reactor vent flow rate.

DETAILED DESCRIPTION OF THE INVENTION

The invention described herein pertains to a novel and improved hydroformylation process, which provides for the benefits of operation in the negative or inverse order region of the hydroformylation rate curve with respect to carbon monoxide, while reducing sudden changes, cycling, and other instability in process parameters, such as reaction rate, total pressure, vent flow rate, and reaction temperature. An important aspect of this novel and improved invention resides in the use of carbon monoxide as a reaction quench gas and fluctuating variable to maintain a predetermined target total pressure in and/or a predetermined target vent flow rate from the hydroformylation reactor, as described in detail hereinafter.

Figure 1:
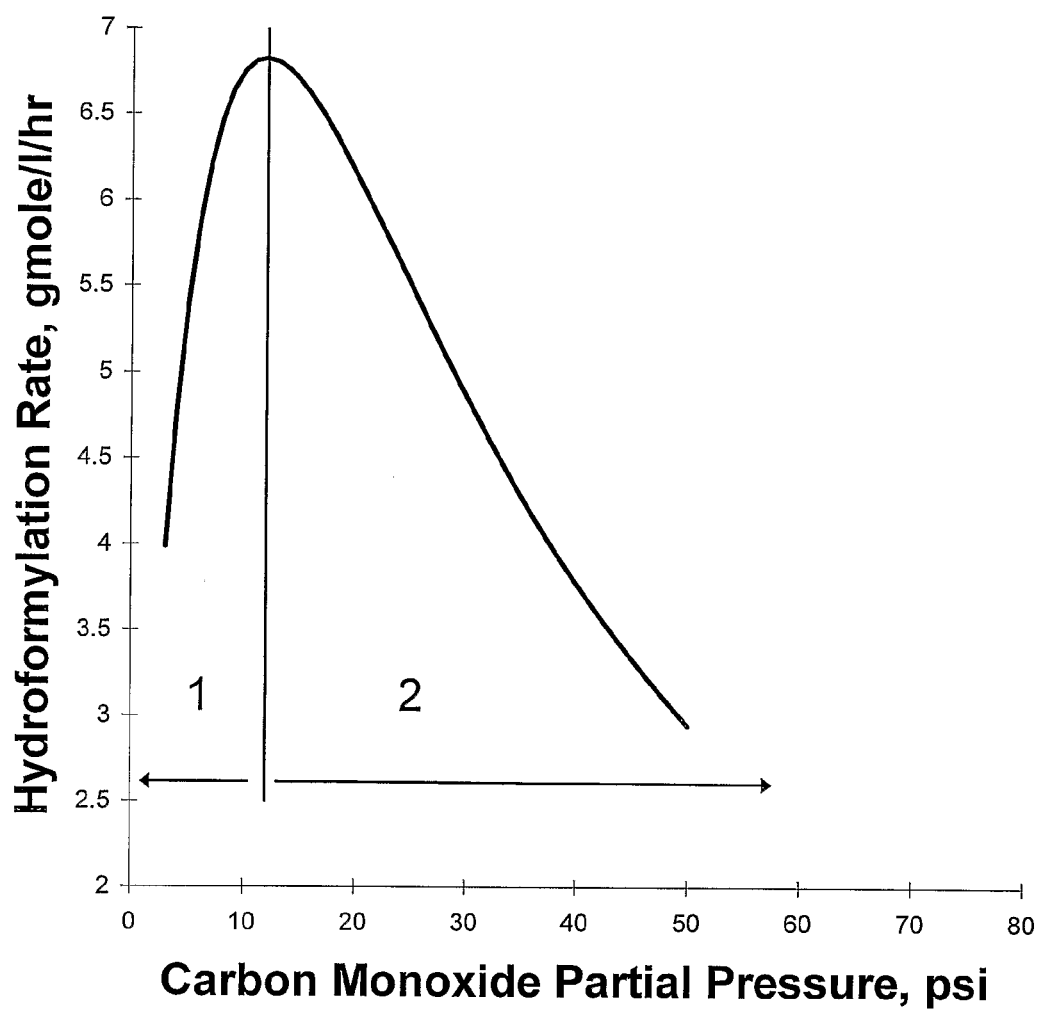
FIG. 1 illustrates a typical graph of Hydroformylation Reaction Rate versus Carbon Monoxide Partial Pressure for a hydroformylation of an olefin with carbon monoxide and hydrogen in the presence of a metal-organopolyphosphite complex catalyst.

As illustration of the problem to be solved, reference is made to FIG. 1, which plots Hydroformylation Reaction Rate versus Partial Pressure of Carbon Monoxide for a theoretical hydroformylation of an unsaturated olefinic compound in the presence of carbon monoxide and hydrogen and a metal-organopolyphosphite hydroformylation catalyst. The essentially inverted U-shaped curve is typical of such processes and generally encompasses two regions: (1) a positive order region wherein the hydroformylation reaction rate increases with an increase in carbon monoxide partial pressure, and wherein the hydroformylation reaction rate decreases with a decrease in carbon monoxide partial pressure; and (2) a negative order region wherein the hydroformylation reaction rate decreases with an increase in carbon monoxide partial pressure, and wherein the hydroformylation reaction rate increases with a decrease in carbon monoxide partial pressure. More specifically, FIG. 1 illustrates that initially reaction rate increases with increasing CO partial pressure; but after reaching a maximum, the reaction rate falls off sharply with increasing CO partial pressure. The sharp change from positive to negative slope occurs as the reaction rate transitions from positive order to negative or inverse order in carbon monoxide. As noted previously, the hydroformylation process is beneficially operated in the negative order region of the hydroformylation rate curve, else the catalyst is degraded through formation of inhibiting and poisoning phosphorus byproducts.

Although operation in the negative order region of the hydroformylation rate curve offers proven benefits, control of operating parameters in this region of the rate curve is considerably more difficult and problematical, to an extent that obtention of reaction rates in the negative order region of the rate curve, as shown in the hypothetical curve of FIG. 1, are difficult to obtain. To illustrate the difficulties, reference is made to FIG. 2, which graphs Total Pressure versus Synthesis Gas Feed Flow Rate at constant vent flow rate for the hydroformylation of propylene (reaction conditions: $H_2$:CO mole ratio, 1.04:1; propylene feed flow, 304 g/h; 75° C.; total constant vent flow rate, 32.67 standard liters per hour (SLH)). The plot illustrates a steadily decreasing total pressure from about 219 psig (1510 kPa) at a syngas feed flow of about 85.34 SLH to about 65 psig (448 kPa) at a syngas feed flow rate of 215.77 SLH. Just barely beyond this syngas feed flow, at only 220.60 SLH, the total pressure jumps dramatically and disproportionately to over 370 psig (2551 MPa). The sharp increase in reaction pressure indicates a sharp decrease in reaction rate and attendant sharp increases in carbon monoxide and hydrogen partial pressures and possibly also a sharp decrease in reaction temperature. The loss of reaction stability occurs at the syngas feed flow at which the process has transitioned from positive order to negative order in carbon monoxide.

Such data as presented hereinabove illustrate the need to control process parameters, such as total pressure, temperature, vent flow rate, and reaction rate, when operating in the region of the rate curve that is negative order in carbon monoxide. The problem outlined hereinabove can be simply and inexpensively solved by application of the invention described herein.

In one aspect, this invention provides for a novel and improved hydroformylation process comprising reacting one or more reactants, carbon monoxide, and hydrogen in the presence of a hydroformylation catalyst to produce a reaction product fluid comprising one or more products, wherein said process is conducted at a carbon monoxide partial pressure such that reaction rate increases as carbon monoxide partial pressure decreases and the reaction rate decreases as carbon monoxide partial pressure increases; and wherein the following process steps are conducted to stabilize reaction rate, total pressure, vent flow rate, temperature, or a combination thereof, the process steps comprising at least one of the following process control schemes selected from:

Scheme A:
(a1) establishing a target total pressure;
(a2) detecting the total pressure, and determining the difference between the detected total pressure and the target total pressure; and
(a3) based on the pressure difference measured in step (a2), manipulating a feed flow of a gas comprising carbon monoxide to adjust the detected total pressure essentially to the target total pressure; and Scheme B:
(b1) establishing a target vent flow rate;
(b2) detecting the vent flow rate, and determining the difference between the detected vent flow rate and the target flow rate; and
(b3) based on the vent flow rate difference measured in step (b2), manipulating a feed flow rate of gas comprising carbon monoxide to adjust the detected vent flow rate essentially to the target vent flow rate.

In an alternative aspect of this invention, process steps (a1) through (a3) and process steps (b1) through (b3) are all be implemented to adjust the detected total pressure essentially to the target total pressure and to adjust the detected vent flow rate essentially to the target vent flow rate.

The term "total pressure" shall be taken to mean the total gas phase pressure of the process comprising the sum of the partial pressures of carbon monoxide, hydrogen, olefin, reaction products, and any inert gases, by-products, and gas phase impurities.

In a preferred embodiment, this invention provides for a novel and improved hydroformylation process comprising reacting one or more olefinic unsaturated compounds with carbon monoxide and hydrogen in the presence of a metal-organophosphorus ligand complex catalyst and optionally free organophosphorus ligand to produce a reaction product fluid comprising one or more aldehydes, wherein said hydroformylation process is conducted at a carbon monoxide partial pressure such that reaction rate increases as carbon monoxide partial pressure decreases and the reaction rate decreases as carbon monoxide partial pressure increases; and wherein the following steps are conducted to float the carbon monoxide partial pressure so as to stabilize reaction rate, total pressure, vent flow rate, reaction temperature, or a combination thereof, the process steps comprising at least one of the following process control schemes selected from:

Scheme A:
(a1) establishing a target total pressure;
(a2) detecting the total pressure, and determining the difference between the detected total pressure and the target total pressure; and
(a3) based on the pressure difference measured in step (a2), manipulating a feed flow of gas comprising carbon monoxide to adjust the detected total pressure essentially to the target total pressure; and Scheme B:
(b1) establishing a target vent flow rate;
(b2) detecting the vent flow rate, and determining the difference between the detected vent flow rate and the target flow rate; and
(b3) based on the vent flow rate difference measured in step (b2), manipulating a feed flow rate of gas comprising carbon monoxide to adjust the detected vent flow rate essentially to the target vent flow rate.

In another aspect of the preferred embodiment, process steps (a1) through (a3) and process steps (b1) through (b3) are all be implemented to adjust the detected total pressure essentially to the target total pressure and to adjust the detected vent flow rate essentially to the target vent flow rate.

In a more preferred embodiment, this invention provides for a novel and improved hydroformylation process comprising reacting in a reaction zone one or more olefinic unsaturated compounds with carbon monoxide and hydrogen in the presence of a metal-organopolyphosphite ligand complex catalyst and optionally a free organopolyphosphite ligand to produce a reaction product fluid comprising one or more aldehydes, and separating in at least one separation zone the one or more aldehydes from the metal-organopolyphosphite ligand complex catalyst and the optional free organopolyphosphite ligand, the improvement comprising: conducting the hydroformylation process at a carbon monoxide partial pressure such that reaction rate increases as carbon monoxide partial pressure decreases and the reaction rate decreases as carbon monoxide partial pressure increases; and wherein the following steps are conducted to float the carbon monoxide partial pressure so as to stabilize reaction rate, total pressure, vent flow rate, reaction temperature, or a combination thereof, the process steps comprising at least one of the following process control schemes selected from:

Scheme A:
(a1) establishing a target total pressure;
(a2) detecting the total pressure, and determining the difference between the detected total pressure and the target total pressure; and
(a3) based on the pressure difference measured in step (a2), manipulating a feed flow of gas comprising carbon monoxide to adjust the detected total pressure essentially to the target total pressure; and Scheme B:
(b 1) establishing a target vent flow rate;
(b2) detecting the vent flow rate, and determining the difference between the detected vent flow rate and the target flow rate; and
(b3) based on the vent flow rate difference measured in step (b2), manipulating a feed flow rate of gas comprising carbon monoxide to adjust the detected vent flow rate essentially to the target vent flow rate.

In this more preferred embodiment, as an alternative, process steps (a1) through (a3) and process steps (b1) through (b3) may be implemented to adjust the detected total pressure essentially to the target total pressure and to adjust the detected vent flow rate essentially to the target vent flow rate.

In another aspect, this invention is a novel apparatus for stabilizing a hydroformylation process comprising:

a reactor comprising a means for feeding one or more reactants; a means for feeding a synthesis gas; optionally, a means for feeding a secondary source of carbon monoxide; a means for feeding a catalyst solution; a means for venting reaction and inert gases; a means for withdrawing a reaction fluid; a means for measuring total gas pressure; and a means for measuring vent flow rate of reaction and inert gases; the apparatus further comprising at least one of the following design schemes selected from:

Design A:
(a1) a means for determining a pressure differential between a target total gas pressure and the measured total gas pressure;
(a2) a means for generating a signal corresponding to the pressure differential;
(a3) a means for receiving the signal from (a2) and for determining and sending an output signal to manipulate the flow rate of synthesis gas and/or secondary source of carbon monoxide to adjust the measured total pressure to the target total pressure; and Design B:
(b1) a means for determining a vent flow rate differential between a target vent flow rate and the measured vent flow rate;
(b2) a means for generating a signal corresponding to the vent flow rate differential;
(b3) a means for receiving the signal from (b2) and for determining and sending an output signal to manipulate the flow rate of synthesis gas and/or secondary source of carbon monoxide to adjust the measured vent flow rate to the target vent flow rate.

In an alternative embodiment, the apparatus may comprise all of design features (a1) through (a3) and design features (b1) through (b3) hereinabove. One skilled in the art is directed to standard references on control systems engineering for description of means for generating signals corresponding to differentials, means for receiving signals, and means for determining and outputting signals to control process variables.

The process invention described hereinabove provides for process stabilization including reduction or elimination of sudden, extreme changes in process parameters and reduction and control over the cycling of reaction parameters, such as hydroformylation reaction rate, total pressure, vent flow rate, reactor temperature, or a combination thereof, during process operation in the sensitive inverse or negative order region of the hydroformylation rate curve with respect to carbon monoxide. In one preferred embodiment of this invention, increased reaction control and stability are achieved, preferably at constant target vent flow rate, by adjusting the flow rate of a carbon monoxide-containing inlet gas to maintain a target total reaction pressure. In another preferred embodiment, reaction control and stability are achieved, preferably at constant target total pressure, by adjusting the flow rate of a carbon monoxide-containing feed gas to maintain a target vent flow rate. Accordingly, the process of this invention allows carbon monoxide partial pressure to float up and down in response to fluctuations in total pressure and/or vent flow rate resulting from fluctuations in the hydroformylation reaction rate, thereby stabilizing the process against sudden and extreme process parameter deviations or cycling thereof. Since in practical operation the process invention manipulates gas flows and total pressure, the process is not impeded by the slow response of manipulating a liquid phase or by the slow response of detecting specific gas component partial pressures. Consequently, the response of the instant process is significantly more rapid than the response of prior art processes.

The hydroformylation process of this invention may be asymmetric or non-asymmetric, the preferred process being non-asymmetric; and may be conducted in any continuous or semi-continuous fashion; and may involve any conventional catalyst liquid and/or gas and/or extraction recycle operation as desired. As used herein, the term "hydroformylation" is contemplated to include all operable asymmetric and non-asymmetric hydroformylation processes that involve converting one or more substituted or unsubstituted olefinic compounds or a reaction mixture comprising one or more substituted or unsubstituted olefinic compounds, typically in the presence of a hydroformylation catalyst, to one or more substituted or unsubstituted aldehydes or a reaction mixture comprising one or more substituted or unsubstituted aldehydes. Any hydroformylation catalyst known in the art may be suitably employed in the process of this invention. Preferably, the hydroformylation catalyst comprises a metal-organophosphorus ligand complex catalyst, wherein the ligand comprises, for example, a triorganophosphite, an organopolyphosphite ligand, or a combination thereof. More preferably, the hydroformylation catalyst comprises a metal-organopolyphosphite ligand complex catalyst. Illustrative metal-organopolyphosphite ligand complex catalyzed hydroformylation processes that are applicable to the invention include, for example, those processes described in U.S. Pat. Nos. 4,148,830; 4,593,127; 4,769,498; 4,717,775; 4,774,361; 4,885,401; 5,264,616; 5,288,918; 5,360,938; 5,364,950; and 5,491,266; the disclosures of which are incorporated herein by reference. Accordingly, the hydroformylation processing techniques applicable to this invention may correspond to any of the processing techniques known and described in the art. Preferred processes are those involving catalyst liquid recycle hydroformylation processes, as described in U.S. Pat. Nos. 4,668,651; 4,774,361; 5,102,505; 5,110,990; 5,288,918; 5,874,639; and 6,090,987; and extractive hydroformylation processes, as described in U.S. Pat. Nos. 5,932,772; 5,952,530; 6,294,700; 6,303,829; 6,303,830; 6,307,109; and 6,307,110; the disclosures of which are incorporated herein by reference.

In general, such catalyzed liquid hydroformylation processes involve the production of aldehydes by reacting an olefinic unsaturated compound with carbon monoxide and hydrogen in the presence of a metal-organophosphorus ligand complex catalyst in a liquid phase that may also contain an organic solvent for the catalyst and ligand. Preferably, free organophosphorus ligand is also present in the liquid phase. By "free organophosphorus ligand" is meant an organophosphorus ligand that is not complexed with (tied to or bound to) the metal, for example, metal atom, of the complex catalyst. Generally, the hydroformylation process may include a recycle method, wherein a portion of the liquid reaction fluid containing the catalyst and aldehyde product is withdrawn from the hydroformylation reactor (which may include one reaction zone or a plurality of reaction zones, for example, in series), either continuously or intermittently; and the aldehyde product is separated and recovered therefrom by techniques described in the art; and then a metal catalyst-containing residue from the separation is recycled to the reaction zone as disclosed, for example, in U.S. Pat. No. 5,288,918. (If a plurality of reaction zones is employed in series, the reactant olefin may be fed to the first reaction zone only; while the catalyst solution, carbon monoxide, and hydrogen may be fed to each of the reaction zones.) As used hereinafter, the term "reaction fluid" or "reaction product fluid" is contemplated to include, but not limited to, a reaction mixture comprising: (a) a metal-ligand complex catalyst, preferably, a metal-organophosphorus ligand complex catalyst, (b) aldehyde product formed in the reaction, (c) optionally, free ligand, (d) optionally, unreacted reactants including unreacted olefin, (e) an organic solubilizing agent for said metal-ligand complex catalyst and said optional free ligand, and (f) optionally, one or more inhibiting or poisoning phosphorus byproducts formed by hydrolysis in the reaction fluid. It is to be understood that the hydroformylation reaction fluid can and normally will contain minor amounts of additional ingredients, such as those that have either been deliberately added or formed in situ during the process. Examples of such additional ingredients include carbon monoxide and hydrogen gases, and in situ formed products, such as saturated hydrocarbons, and/or unreacted isomerized olefins corresponding to the olefin starting materials, and/or high boiling liquid aldehyde condensation byproducts, as well as other inert co-solvents or hydrocarbon additives, if employed.

As stated above, the subject invention resides in the discovery that deactivation of the metal-organophosphorus ligand complex catalyst caused by inhibiting or poisoning phosphorus byproducts can be reversed or at least reduced by carrying out the hydroformylation process in a reaction region where the hydroformylation reaction rate is of a negative or inverse order in carbon monoxide; and moreover, sudden changes in or cycling of hydroformylation reaction rate, total pressure, vent flow rate, temperature, or a combination thereof in the negative or inverse region of the reaction rate curve can be prevented and/or reduced by floating the carbon monoxide partial pressure to maintain either a targeted total pressure, or a targeted vent flow rate, or both.

Figure 3:
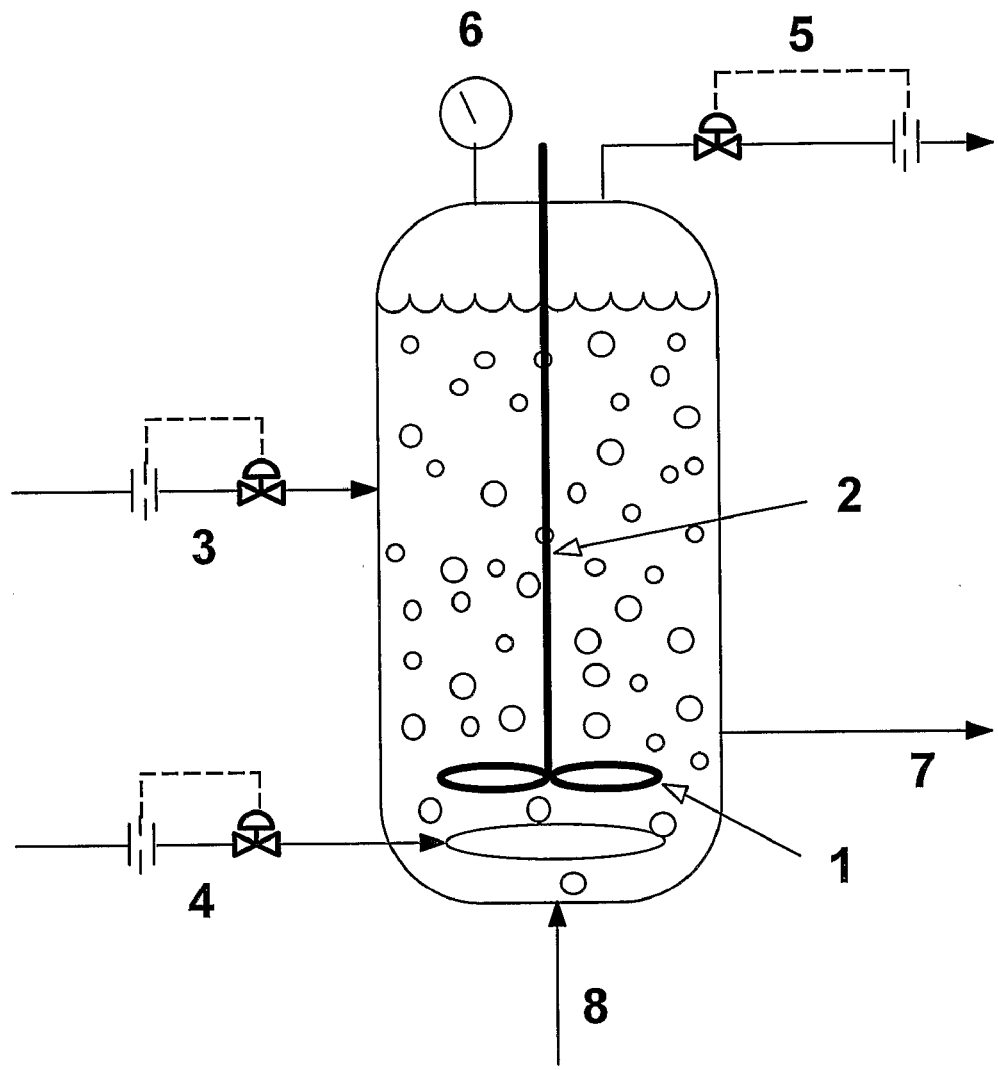
FIG. 3 illustrates a continuous hydroformylation reactor with olefin, syngas, and vent flow controls, the reactor configured for the process illustrated in FIG. 2.

Selection of an operable target total pressure constitutes an important aspect in this invention. In this regard, reactor design may affect the selection. Preferably, a reactor design is employed that allows for steady-state operation during data collection. A continuous liquid recycle hydroformylation design is shown in FIG. 3. Such a reactor is preferably equipped with an impeller (1), impeller shaft (2), olefin feed line and flow control (3), syngas feed line and flow control (4), a vent line and vent flow control (5), a total pressure sensor (6), an exit line for removing product solution from the reactor (7), and an entry line for feeding recovered catalyst back to the reactor (8). The syngas feed line typically terminates in the reactor with a sparger. Optionally, the reactor may include one or more baffles (not shown in figure) that separate the inner chamber of the reactor into a plurality of reaction zones. Typically, each baffle is attached to the inner wall of the reactor and extends into the reactor perpendicular to the impeller shaft; and each baffle contains an opening or hole of sufficient size for passage of the impeller shaft as well as reaction fluid and gases. Typically, each chamber or zone in the reactor formed by such baffles contains an impeller as well as a gas sparger for circulating and mixing the reaction fluid in that chamber or zone.

For illustrative purposes, the selection of an operable target total pressure is discussed with reference to FIG. 2 using the apparatus configured as in FIG. 3. At the start, a variety of process parameters are selected, including a specific unsaturated olefinic compound or mixture of olefinic compounds, a specific hydroformylation catalyst, preferably, a metal-organophosphorus ligand complex catalyst, optionally excess ligand, a solvent, a reaction temperature, an olefin feed rate, and a syngas $H_2$:CO mole ratio. An initial syngas feed rate is selected that is stoichiometrically less than the olefin feed rate, preferably, less than ½ the stoichiometric feed rate relative to the olefin feed rate. A vent flow rate from the reactor is also selected. Typically, all variables are fixed, with the exception of syngas feed flow rate and total pressure.

Figure 2:
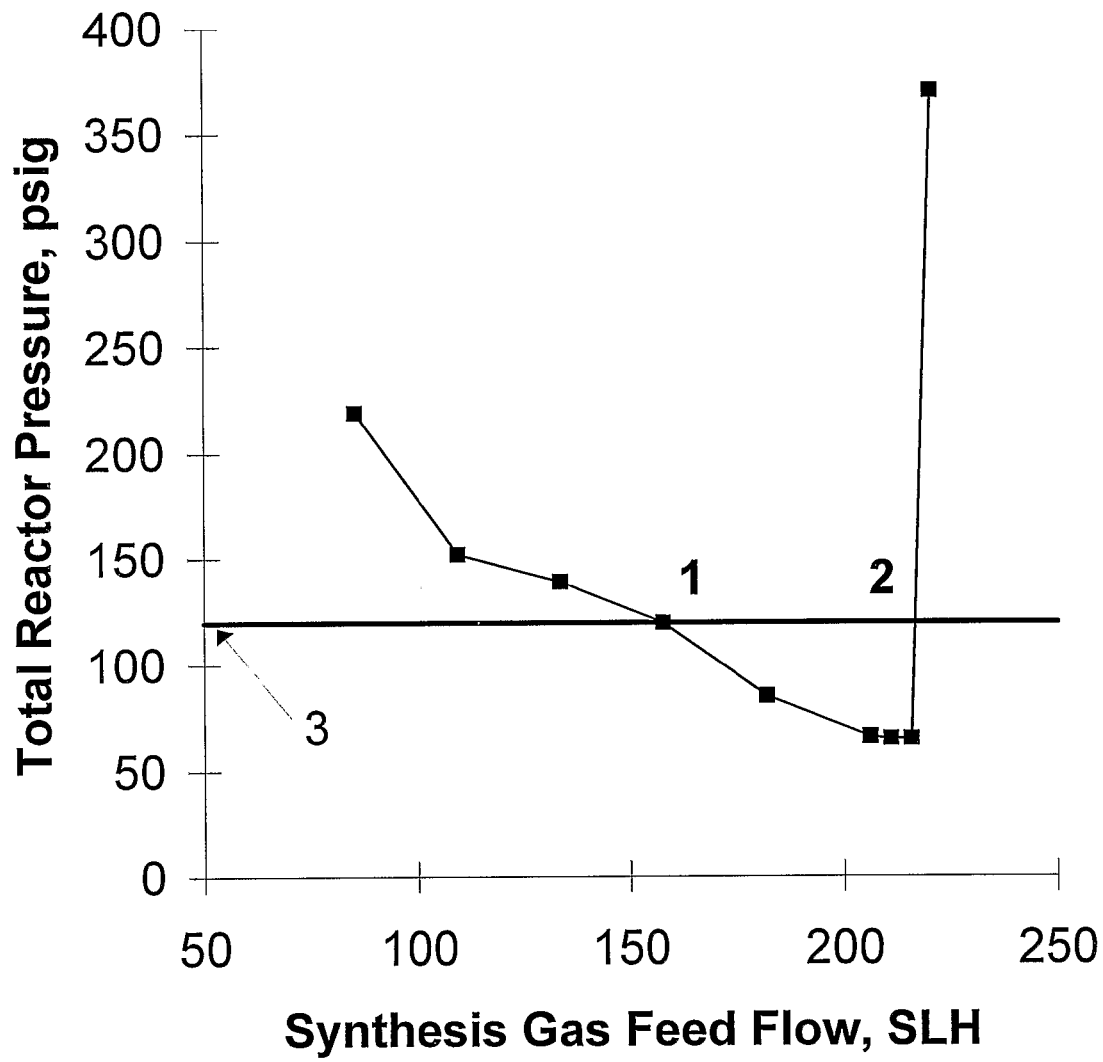
FIG. 2 illustrates a graph of Total Reactor Pressure versus Synthesis Gas Feed Flow Rate at constant vent flow rate for a hydroformylation reaction. This graph also illustrates the method of selecting minimum and maximum primary carbon monoxide or syngas feed flow rates in accordance with the invention.

With reference to FIG. 2, the syngas feed flow is started, and after the reaction reaches a steady-state operation, the total pressure is detected and recorded. In the initial phase of this evaluation, excess olefin feed is present, and the reaction system is rate limited by the sub-stoichiometric synthesis gas feed. Thus, as the syngas feed flow increases at fixed olefin feed rate (and because typically initially the reaction is positive order in carbon monoxide), the total system pressure steadily declines as more carbon monoxide and hydrogen are available to satisfy the stoichiometry of the hydroformylation reaction. The total pressure continues to decline, until a point is reached wherein the carbon monoxide partial pressure is sufficiently high to cross into the negative order region of the rate curve. When that point is reached, the total pressure climbs suddenly and dramatically since each increment of additional carbon monoxide partial pressure slows, or quenches, the hydroformylation rate. Desirable target total pressures are selected from the range of total pressures measured in the negative order region of the curve (FIG. 2, steeply rising positive slope with increasing syngas feed flow and CO partial pressure).

Once a target total pressure is selected as described hereinabove, then in one embodiment of the invention the actual pressure during the hydroformylation process is intermittently or preferably continuously monitored using standard pressure detection means, and the difference between the target total pressure and the actual total pressure is calculated. Thereafter, reaction stability is achieved by adjusting the flow rate of a carbon monoxide inlet gas either upward or downward to reset the measured pressure to the target total pressure, preferably, while maintaining a target vent flow rate. (Determination of target vent flow rate is described hereinafter.) Thus, if the actual pressure is high relative to the target pressure, which implies an insufficient hydroformylation rate, the flow rate of carbon monoxide-containing gas is dropped back. If the measured pressure is low relative to the target pressure, which implies an unacceptably fast hydroformylation rate, the flow rate of carbon monoxide-containing gas is ramped up.

Total pressure is suitably measured by any conventional pressure detection means, which may be located in the syngas feed source line just prior to the syngas inlet to the reactor, or alternatively, located in the reactor itself, or in a vent line exiting from the reactor. The carbon monoxide-containing gas may be fed to the reactor in any manner, satisfying the conditions that the reaction is conducted in a region that is negative order in carbon monoxide and that total pressure is maintained constant by adjusting the flow rate of a carbon monoxide-containing gas, preferably, at the target reactor vent flow rate. In one embodiment of the invention, shown in FIG. 4, a primary feed flow of synthesis gas (4) is varied to control reactor pressure. Particularly desirable results are obtained by setting a minimum primary carbon monoxide-containing gas flow (that is, syngas flow) (4), and then adjusting the total pressure to the target pressure with a secondary feed of a carbon monoxide-containing gas (9). In the aforementioned mode of operation, other process conditions, such as the reactant (for example, olefin) feed rate, reactant feed composition, syngas feed composition, liquid level, rate of agitation, rate of withdrawal of reaction fluid, rate of recycle of catalyst solution, temperature, and the vent flow rate are, more preferably, set at essentially constant values.

Figure 4:
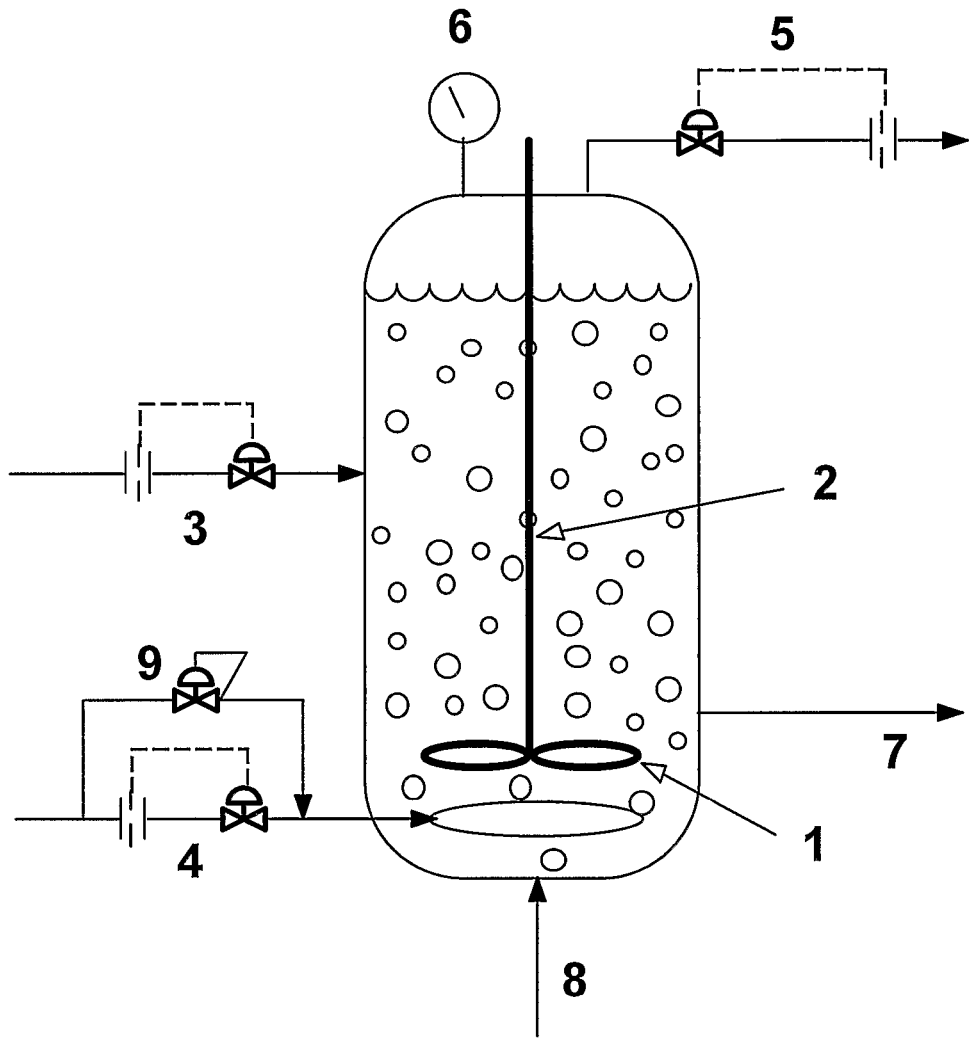
FIG. 4 illustrates a continuous hydroformylation reactor with olefin and vent flow controls, and in accordance with the invention, primary and secondary syngas feed flow controls for controlling total reactor pressure.

The latter method, wherein primary and secondary carbon monoxide feed flows are utilized, can be illustrated with FIG. 4 using information obtained from the data illustrated in FIG. 2. In this method, a target total pressure is selected along the steeply rising positive slope of the curve. (for example, FIG. 2, Point 3) Thereafter, a minimum primary carbon monoxide-containing gas flow rate is selected as about the minimum carbon monoxide feed flow rate corresponding to the target total pressure (FIG. 2, Point 1, first intersection of total pressure curve with flat-line target total pressure). Preferably, a higher syngas or carbon monoxide feed flow rate is desirably employed to ensure that the system does not stabilize in the positive order region of the rate curve. While operating with a suitable minimum primary carbon monoxide flow rate where the total pressure is less than the desired target pressure, a secondary, typically incremental, flow of a carbon monoxide-containing gas (FIG. 4 (9)) is fed to the reactor to adjust the total pressure to the target value. With addition of carbon monoxide from a secondary feed flow, the total pressure will move even lower until the minimum point is achieved, as shown in FIG. 2. Past the minimum, the reaction enters the region of steeper slope which is negative order in carbon monoxide; however, the secondary carbon monoxide flow, as seen in the design of FIG. 4 (9), will act as a quench agent in this region, thereby providing rapid and sensitive reaction control. Thus, as carbon monoxide is consumed and the reaction rate speeds up, additional carbon monoxide is added to quench and stabilize the reaction. In this manner, as illustrated in FIG. 4, the carbon monoxide feed and partial pressure are not constant, but rather float up and down to maintain the total pressure as close as possible to the target total pressure. As shown in FIG. 2 (Point 2), the maximum primary carbon monoxide-containing gas flow rate may preferably be chosen at the second intersection of the reactor total pressure with the target total pressure.

Preferably, synthesis gas is used to provide the primary source of carbon monoxide-containing gas feed. (See FIG. 4 (4).) A separate stream of pure carbon monoxide or carbon monoxide-containing gas, for example, syngas, can provide the secondary reaction quench gas source. (See FIG. 4 (9) or FIG. 13 (12).) Suitable carbon monoxide-containing gases include carbon monoxide mixtures with hydrogen, syngas, nitrogen, helium, argon, and/or methane, and mixtures thereof. Separate gas flow controls may be provided for the primary and secondary flows, or in the case where the secondary flow uses synthesis gas as the carbon monoxide-containing gas, a single flow meter may be used with appropriate process controls.

In the aforementioned embodiment, an adjusting amount of carbon monoxide-containing gas is fed to the reactor from a secondary carbon monoxide source to control total pressure at a predetermined target value. The reactor vent flow may be kept constant, but measured and controlled independently, for example, by an orifice meter measuring the flow and a control means, that is, valve, controlling the flow rate through the vent orifice meter. The term "valve" shall refer to any one of numerous devices by which the flow of a gas may be started, stopped, or regulated, typically, by a movable part that opens, shuts, or partially obstructs one or more ports or passageways, including, but not limited to, globe, gate, needle, plug (cock), butterfly, poppet, and spool valves.

When operating the process as disclosed herein, to the extent that the ratio of hydrogen to carbon monoxide being fed is different from the stoichiometry of hydroformylation and byproduct olefin hydrogenation, the excess gas and the byproduct gas should be vented to maintain process productivity. Otherwise, at a predetermined total process pressure, an increasing fraction of the total process pressure will be devoted to undesired or less desirable components. In a similar manner, impurities in synthesis gas including methane, carbon dioxide, nitrogen or other inerts or gaseous inerts in the olefin feed can accumulate and lower process productivity. These impurities also need to be vented.

Thus, in another preferred embodiment of this invention, reaction stability can be controlled by means of vent flow rate. (FIG. 19) In such an embodiment, the flow rate of a carbon monoxide-containing gas fed to the reactor (FIG. 19 (14)) is used to adjust the reactor vent flow rate to a target vent flow rate, preferably, while maintaining the target total pressure. Target vent flow rate is determined by monitoring the effluent stream from the reactor (FIG. 19 (11)), and choosing a vent flow rate that maximizes release of inerts, such as hydrogen and impurity gases and minimizes release of reactant olefin and, optionally, syngas. Standard gas chromatography techniques may be suitably employed for analysis of the vent stream. A minimum target vent rate is that which will remove excess hydrogen and impurity gases at essentially the rate that they are being introduced, recognizing of course that some of the inerts, such as saturated hydrocarbon formed by hydrogenation of olefin or inerts fed with an olefin, may also exit dissolved in the catalyst solution. Target vent rates higher than the minimum are also permissible, but at the cost of reduced process efficiency. In accordance with the invention, as the measured vent flow rate fluctuates from the target vent flow rate, then the carbon monoxide-containing feed gas is varied to adjust the measured vent flow rate back to the target vent rate. In practice, an increasing vent flow rate above the target vent flow rate results in a decrease in carbon-monoxide-containing feed gas rate, and a decrease in vent flow rate below the target vent rate results in an increase in carbon monoxide-containing feed gas rate. In this preferred embodiment, more preferably, other process conditions, such as the reactant (for example, olefin) feed rate, reactant feed composition, syngas feed composition, liquid level, rate of agitation, rate of withdrawal of reaction fluid, rate of recycle of catalyst solution, temperature and the total pressure are set at essentially constant values.

Both the first and second preferred embodiments of this invention have several aspects in common. A minimum carbon monoxide-containing feed gas flow is typically controlled using a primary carbon monoxide source and using predetermined operational parameters taken from the graph of Total Pressure versus Synthesis Gas Feed Flow Rate (FIG. 2). The total pressure (control 1) and the reactor vent flow rate (control 2) are individually or both controlled at constant predetermined target values (2 controlled variables). Two control means (or equivalents; for example, valves) are typically provided, one means on the secondary carbon monoxide-containing feed gas and another means on the reactor vent line (2 manipulated variables). The main difference between the two embodiments is that in the first design the total pressure is measured, whereas in the second design the vent flow rate is measured. Either measurement is transmitted via an appropriate signaling means to the carbon monoxide feed line, preferably, a secondary carbon monoxide feed line, to adjust the total pressure to the target pressure or to adjust the vent flow rate to the target vent flow rate. Preferably, the adjustments are made as close as practically possible to the target pressure and target vent flow rate within the design limitations.

In a third preferred embodiment of this invention, aspects of the first and second preferred embodiments are combined. The total pressure and the reactor vent flow rate (2 controlled variables) are both controlled at predetermined target values using two control means (that is, valves or equivalents), one means on the carbon monoxide-containing feed gas and another means on the reactor vent line (2 manipulated variables). The appropriately combined measurements are transmitted via appropriate signaling means to the carbon monoxide feed line, preferably, a secondary carbon monoxide feed line, and reactor vent flow line to adjust the total pressure to the target pressure and to adjust the vent flow rate to the target vent flow rate.

When the hydroformylation process is conducted in a plurality of continuous stirred tank reactors connected in series, the vent flow rate and/or reactor pressure from one or more of the reactors in series can be used to estimate the total vent flow rate and/or pressure over the plurality of reactors in series, and the measurement(s) can then be transmitted to a carbon monoxide-containing gas (for example, syngas) entry line at the first reactor or any other reactor or combination of reactors to adjust the total pressure and/or vent flow rate over the entire series of reactors to the target total pressure or target vent flow rate, or combination thereof.

As another option, a portion of the total vent gases from the reactor, with or without further separation or purification, may be recycled as feed to the reactor.

Unexpectedly, by the method of this invention the hydroformylation process can be simply, inexpensively, and effectively controlled in the negative or inverse order region of the rate curve with respect to carbon monoxide, where highly desirable normal to branched aldehyde isomer ratios and ligand/catalyst stability are enhanced, but where otherwise, until the present discovery, process control has been a challenge. Moreover, it is possible by means of this invention to select and operate in a region of optimal carbon monoxide partial pressure in the inverse order region of the rate curve. Preferably, carbon monoxide partial pressures are chosen that achieve a hydroformylation reaction rate at the maximum or within 50 percent of the maximum (peak) reaction rate, more preferably, at or within 30 percent of the peak reaction rate, and most preferably, at or within 10 percent of the peak reaction rate, as determined by a plot of hydroformylation reaction rate versus carbon monoxide partial pressure.

With reference to suitable hydroformylation process conditions, illustrative metal-ligand complex catalysts employable in the hydroformylation process of this invention, as well as methods for their preparation, are well known in the art and include those disclosed in the above mentioned referenced patents. In general, such catalysts may be preformed or formed in situ and consist essentially of metal in complex combination, typically, with an organophosphorus ligand, preferably, an organopolyphosphite ligand. It is believed that carbon monoxide is also present and complexed with the metal in the active species, which also may contain hydrogen directly bonded to the metal.

The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, and most preferably, rhodium. Other permissible metals include Group 6 metals selected from chromium (Cr), molybdenum (Mo), tungsten (W) and mixtures thereof. Mixtures of metals from Groups 6, 8, 9 and 10 may also be used in this invention.

Preferred organopolyphosphite ligands that make up the metal-organopolyphosphite ligand complexes and free organopolyphosphite ligand include mono-, di-, tri- and higher organopolyphosphites. Mixtures of such ligands may be employed if desired in the metal-organopolyphosphite ligand complex catalyst and/or free ligand, and such mixtures may be the same or different.

The term "complex" as used herein and in the claims means a coordination compound formed by the union of one or more electronically rich molecules or atoms with one or more electronically poor molecules or atoms. For example, the organopolyphosphite ligands employable herein possess two or more phosphorus donor atoms, each having one available or unshared pair of electrons, which are each capable of forming a coordinate covalent bond independently or possibly in concert (for example, via chelation) with the metal. Carbon monoxide can also be present and complexed with the metal. The ultimate composition of the complex catalyst may also contain an additional ligand, for example, hydrogen or an anion satisfying the coordination sites or nuclear charge of the metal. Illustrative additional ligands include, for example, halogen (Cl, Br, I), allyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, for example, alkyl or aryl), acetate, acetylacetonate, $SO_4$, $PF_4$, $PF_6$, $NO_2$, $NO_3$, $CH_3O$, $CH_2$=$CHCH_2$, $CH_3CH$=$CHCH_2$, $C_2H_5CN$, $CH_3CN$, $NH_3$, pyridine, $(C_2H_5)_3N$, mono-olefins, diolefins and triolefins, tetrahydrofuran, and the like.

The number of available coordination sites on such metals is well known in the art. Thus the catalytic species may comprise a complex catalyst mixture, in their monomeric, dimeric or higher nuclearity forms, which are preferably characterized by at least one organophosphorus-containing molecule complexed per one molecule of metal, for example, rhodium. For instance, it is considered that the catalytic species of the preferred catalyst employed in the hydroformylation reaction may be complexed with carbon monoxide and hydrogen in addition to the organophosphorus ligand(s) in view of the carbon monoxide and hydrogen gas employed by the hydroformylation reaction.

The preferred organopolyphosphites that may serve as the ligand of the metal-organopolyphosphite ligand complex catalyst and/or free ligand of the hydroformylation processes and reaction product fluids of this invention may be achiral (optically inactive) or chiral (optically active) and are well known in the art. Achiral organopolyphosphites are preferred. Representative organopolyphosphites contain two or more tertiary (trivalent) phosphorus atoms and may include those having the formula:

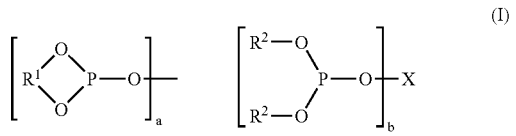

(I)

wherein X represents a substituted or unsubstituted n-valent organic bridging radical containing from 2 to 40 carbon atoms, each $R^1$ is the same or different and represents a divalent organic radical containing from 4 to 40 carbon atoms, each $R^2$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^1$ radical may be the same or different, and when b has a value of 1 or more, each $R^2$ radical may be the same or different.

Representative n-valent (preferably divalent) hydrocarbon bridging radicals represented by X and representative divalent organic radicals represented by $R^1$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, and the like, wherein each y is the same or different and is a value of 0 or 1. Q represents a divalent bridging group selected from —$C(R^3)_2$—, —O—, —S—, —$NR^4$—, —Si$(R^5)_2$— and —CO—, wherein each $R^3$ is the same or different and represents hydrogen, an alkyl radical having from 1 to 12 carbon atoms, phenyl, tolyl, and anisyl, $R^4$ represents hydrogen or a substituted or unsubstituted monovalent hydrocarbon radical, for example, an alkyl radical having 1 to 4 carbon atoms; each $R^5$ is the same or different and represents hydrogen or an alkyl radical, and m is a value of 0 or 1. The more preferred acyclic radicals represented by X and $R^1$ above are divalent alkylene radicals, while the more preferred aromatic radicals represented by X and $R^1$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616; 5,364,950; 5,874,640; 5,892,119; 6,090,987; and 6,294,700 and the like, the disclosures of which are incorporated herein by reference. Representative preferred monovalent hydrocarbon radicals represented by each $R^2$ radical above include alkyl and aromatic radicals.

Illustrative preferred organopolyphosphites may include bisphosphites such as those of Formulas (II) to (IV) below:

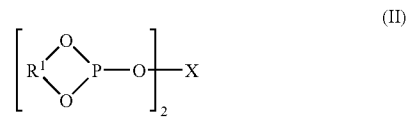

(II)

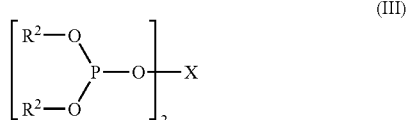

(III)

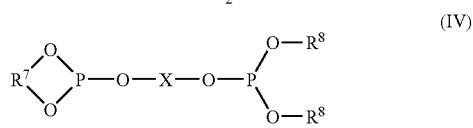

(IV)

wherein each $R^1$, $R^2$ and X of Formulas (II) to (IV) is the same as defined above for Formula (I). Preferably each $R^1$ and X represent a divalent hydrocarbon radical selected from alkylene, arylene, arylene-alkylene-arylene, and bisarylene, while each $R^2$ radical represents a monovalent hydrocarbon radical selected from alkyl and aryl radicals. Organopolyphosphite ligands of such Formulas (II) to (IV) may be found disclosed, for example, in U.S. Pat. Nos. 4,668,651; 4,748, 261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following Formulas (V) to (VII):

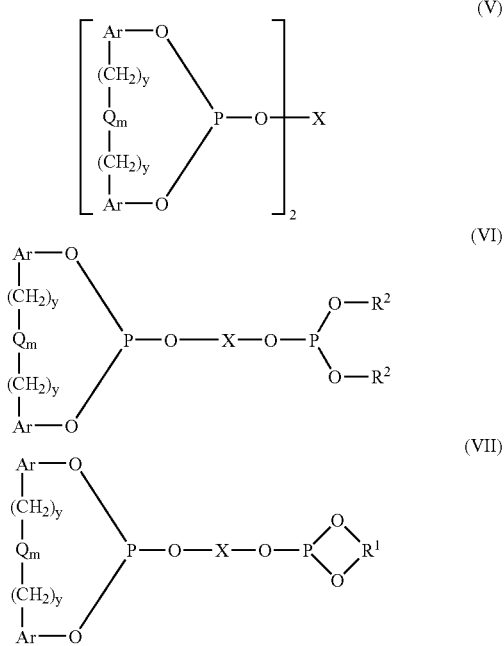

wherein Q, $R^1$, $R^2$, X, m, and y are as defined above, and each Ar is the same or different and represents a substituted or unsubstituted aryl radical. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —C($R^3$)$_2$ where each $R^3$ is the same or different and represents hydrogen or a methyl radical. More preferably each alkyl radical of the above defined $R^2$ groups may contain from 1 to 24 carbon atoms and each aryl radical of the above-defined Ar, X, $R^1$ and $R^2$ groups of the above Formulas (V) to (VII) may contain from 6 to 18 carbon atoms and said radicals may be the same or different, while the preferred alkylene radicals of X may contain from 2 to 18 carbon atoms and the preferred alkylene radicals of $R^1$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organopolyphosphite in the above Formulas (I) to (VII) may be an ionic phosphite, that is, may contain one or more ionic moieties selected from the group consisting of: —$SO_3M$, wherein M represents an inorganic or organic cation, —$PO_3M$ wherein M represents an inorganic or organic cation, N($R^6$)$_3X^1$, wherein each $R^6$ is the same or different and represents a hydrocarbon radical containing from 1 to 30 carbon atoms, for example, alkyl, aryl, alkaryl, aralkyl, and cycloalkyl radicals, and $X^1$ represents inorganic or organic anion, —$CO_2$ M wherein M represents inorganic or organic cation, as described, for example, in U.S. Pat. Nos. 5,059,710; 5,113,022 5,114,473; and 5,449,653; the disclosures of which are incorporated herein by reference. Thus, if desired, such organopolyphosphite ligands may contain from 1 to 3 such ionic moieties, while it is preferred that only one such ionic moiety be substituted on any given aryl moiety in the organopolyphosphite ligand when the ligand contains more than one such ionic moiety. As suitable counter-ions, M and $X^1$, for the anionic moieties of the ionic organopolyphosphites there can be mentioned hydrogen (that is a proton), the cations of the alkali and alkaline earth metals, for example, lithium, sodium, potassium, cesium, rubidium, calcium, barium, magnesium and strontium, the ammonium cation and quaternary ammonium cations, phosphonium cations, arsonium cations and iminium cations. Suitable anionic atoms of radicals include, for example, sulfate, carbonate, phosphate, chloride, acetate, oxalate and the like.

Of course any of the $R^1$, $R^2$, X, Q and Ar radicals of such non-ionic and ionic organopolyphosphites of Formulas (I) to (VII) above may be substituted if desired, with any suitable substituent containing from 1 to 30 carbon atoms that does not adversely affect the desired result of the process of this invention. Substituents that may be on said radicals in addition of course to corresponding hydrocarbon radicals such as alkyl, aryl, aralkyl, alkaryl and cyclohexyl substituents, may include for example silyl radicals such as —Si($R^7$)$_3$; amino radicals such as —N($R^7$)$_2$; phosphine radicals such as -aryl-P($R^7$)$_2$; acyl radicals such as —C(O)$R^7$; acyloxy radicals such as —OC(O)$R^7$; amido radicals such as —CON($R^7$)$_2$ and —N($R^7$)COR$^7$; sulfonyl radicals such as —$SO^2R^7$, alkoxy radicals such as —O$R^7$; sulfinyl radicals such as —SO$R^7$; sulfenyl radicals such as —S$R^7$; phosphonyl radicals such as —P(O)($R^7$)$_2$; as well as halogen, nitro, cyano, trifluoromethyl, hydroxy radicals, and the like, wherein each $R^7$ radical individually represents the same or different monovalent hydrocarbon radical having from 1 to 18 carbon atoms (for example, alkyl, aryl, aralkyl, alkaryl and cyclohexyl radicals), with the proviso that in amino substituents such as —N($R^7$)$_2$ each $R^7$ taken together can also represent a divalent bridging group that forms a heterocyclic radical with the nitrogen atom, and in amido substituents such as —C(O)N($R^7$)$_2$ and —N($R^7$)COR$^7$ each $R^7$ bonded to N can also be hydrogen. Of course it is to be understood that any of the substituted or unsubstituted hydrocarbon radicals groups that make up a particular given organopolyphosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —O(CH$_2$CH$_2$)$_2$OCH$_3$, —O(CH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$ C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)

($C_2H_5$)$_2$, —P(O)($C_3H_7$)$_2$, —P(O)($C_4H_9$)$_2$, —P(O)($C_6H_{13}$)$_2$, —P(O)CH$_3$($C_6H_5$), —P(O)(H)($C_6H_5$), and the like.

Specific illustrative examples of such organobisphosphite ligands include the following:

6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

Ligand A

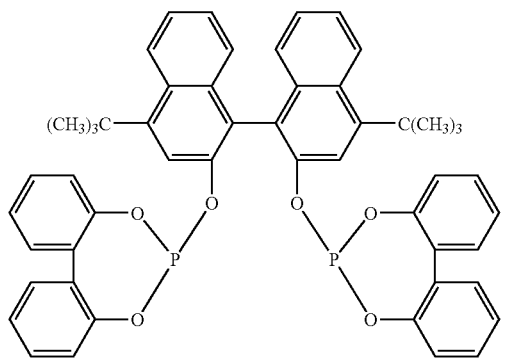

6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin having the formula:

Ligand B

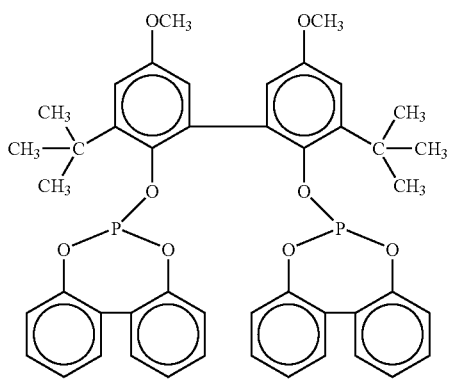

6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

Ligand C

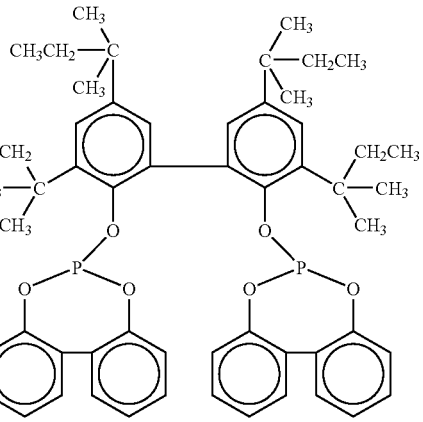

6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin having the formula:

Ligand D

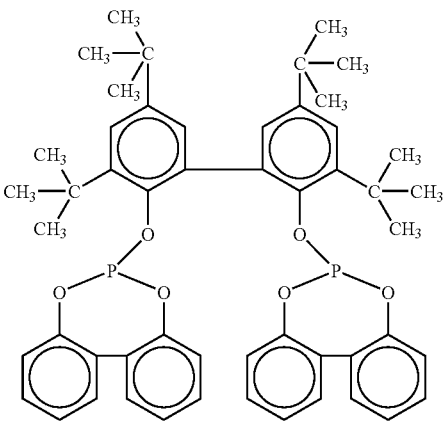

(2R,4R)-di[2,2'-(3,3',5,5'-tetrakis-tert-amyl-1,1'-biphenyl)]-2,4-pentyldiphosphite having the formula:

Ligand E

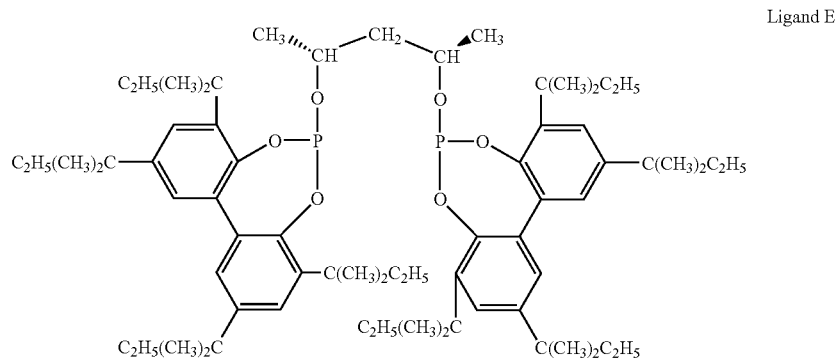

(2R,4R)-di[2,2'-(3,3',5,5'-tetrakis-tert-butyl-1,1'-biphenyl)]-2,4-pentyldiphosphite having the formula:

(2R,4R)-di[2,2'-(3,3'-di-tert-butyl-5,5'-diethoxy-1,1'-biphenyl)]-2,4-pentyldiphosphite having the formula:

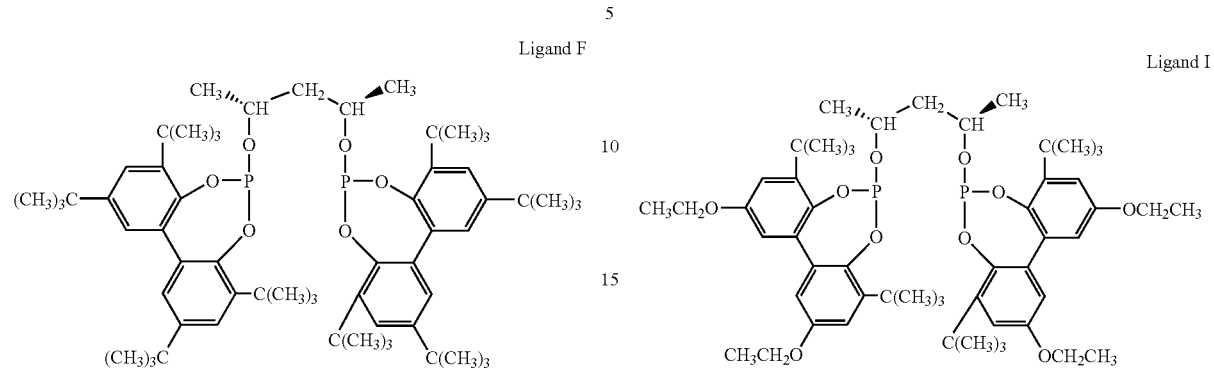

(2R,4R)-di[2,2'-(3,3'-di-amyl-5,5'-dimethoxy-1,1'-biphenyl)]-2,4-pentyldiphosphite having the formula:

(2R,4R)-di[2,2'-(3,3'-di-tert-butyl-5,5'-diethyl-1,1'-biphenyl)]-2,4-pentyldiphosphite having the formula:

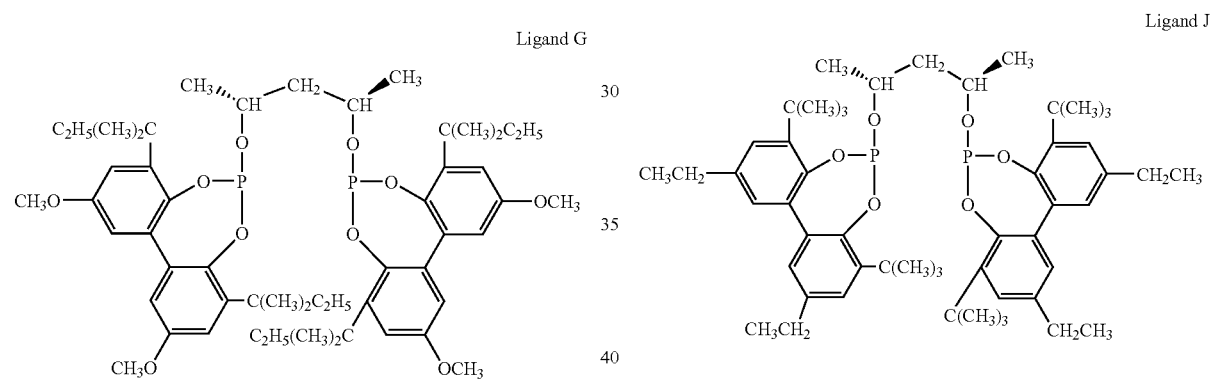

(2R,4R)-di[2,2'-(3,3'-di-tert-butyl-5,5'-dimethyl-1,1'-biphenyl)]-2,4-pentyldiphosphite having the formula:

(2R,4R)-di[2,2'-(3,3'-di-tert-butyl-5,5'-dimethoxy-1,1'-biphenyl)]-2,4-pentyldiphosphite having the formula:

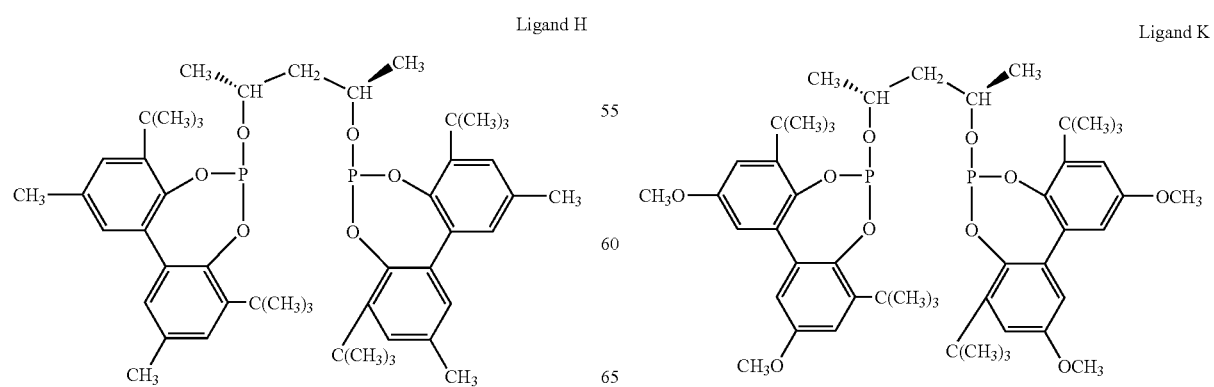

6-[[2'-[(4,6-bis(1,1-dimethylethyl)-1,3,2-benzodioxaphos-phol-2-yl)oxy]-3,3'-bis(1,1-dimethylethyl)-5,5'-dimethoxy[,1'-biphenyl]-2-yl]oxy]-4,8-bis(1,1-dimethylethyl)-2,10-dimethoxydibenzo[d,f][1,3,2]dioxa-phosphepin having the formula:

Ligand L

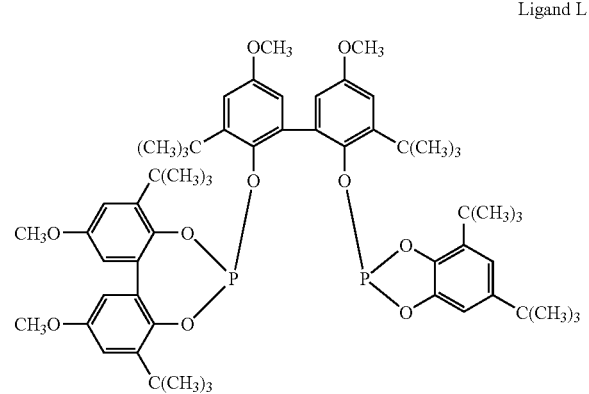

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand M

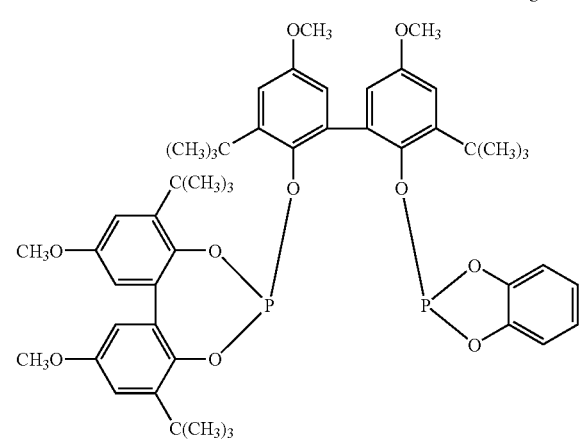

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand N

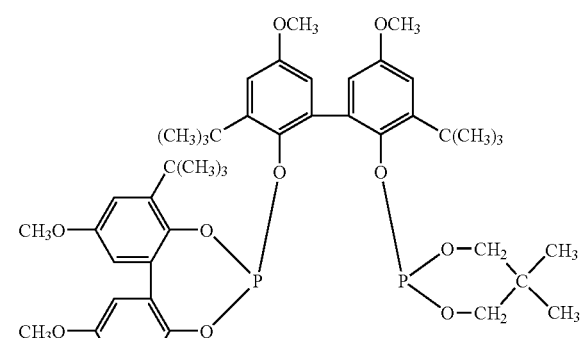

2'-[[4,8-bis(1,1-dimethylethyl)-2,10-dimethoxydibenzo[d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

Ligand O

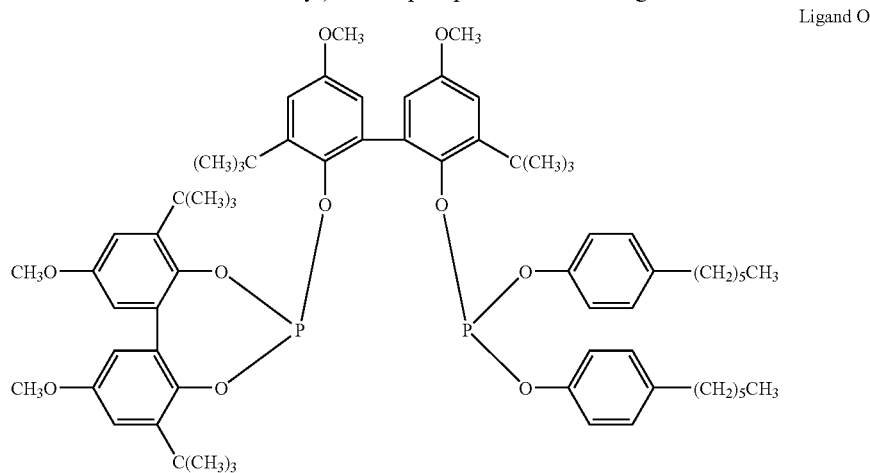

2-[[2-[[4,8,-bis(1,1-dimethylethyl), 2,10-dimethoxy-dibenzo-[d,f][1,3,2]dioxophosphepin-6-yl]oxy]-3-(1,1-dimethylethyl)-5-methoxyphenyl]methyl]-4-methoxy, 6-(1,1-dimethylethyl)phenyl diphenyl ester of phosphorous acid having the formula:

Ligand P

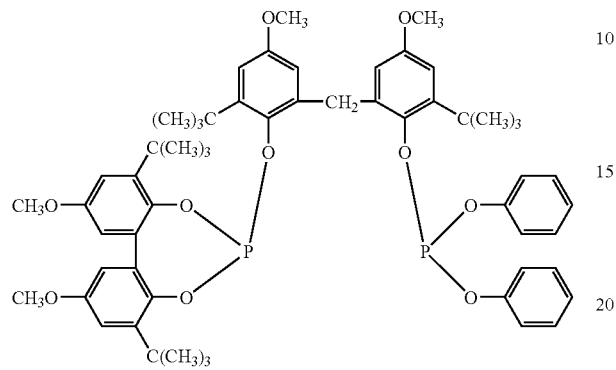

3-methoxy-1,3-cyclohexamethylene tetrakis[3,6-bis(1,1-dimethylethyl)-2-naphthalenyl]ester of phosphorous acid having the formula:

Ligand Q

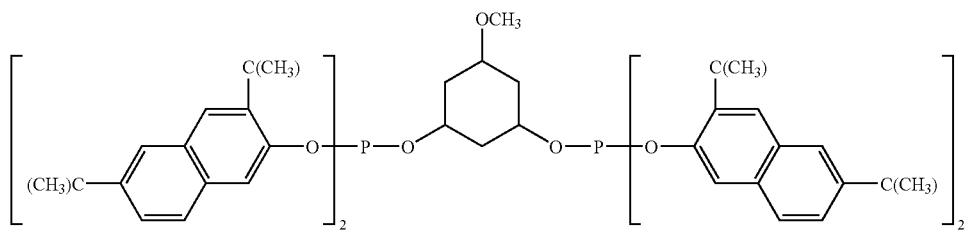

2,5-bis(1,1-dimethylethyl)-1,4-phenylene tetrakis[2,4-bis(1,1-dimethylethyl)phenyl]ester of phosphorous acid having the formula:

Ligand R

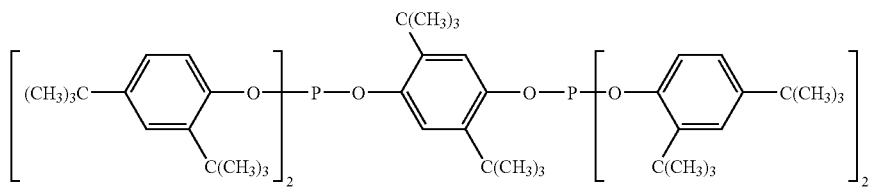

methylenedi-2,1-phenylene tetrakis[2,4-bis(1,1-dimethylethyl)phenyl]ester of phosphorous acid having the formula:

Ligand S

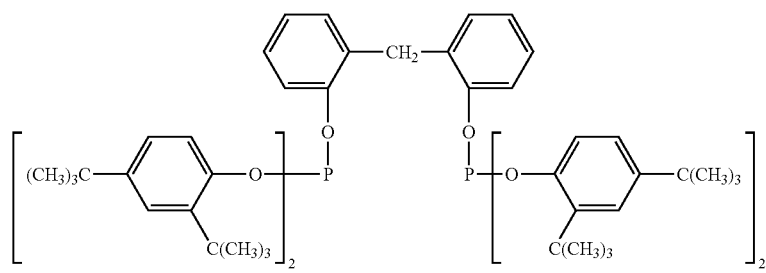

[1,1'-biphenyl]-2,2'-diyl tetrakis[2-(1,1-dimethylethyl)-4-methoxyphenyl]ester of phosphorous acid having the formula:

Ligand T

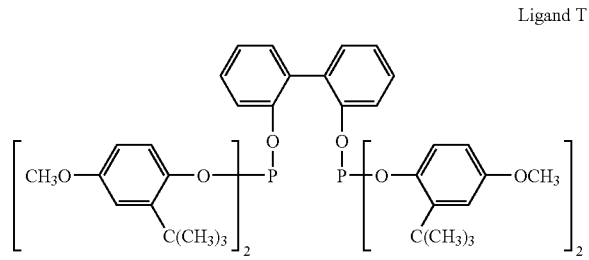

The amount of metal-ligand complex catalyst present in the reaction fluid of the hydroformylation process of this invention need only be that minimum amount necessary to provide the given metal concentration desired and necessary to catalyze the selected hydroformylation process. In general, metal, for example, rhodium, concentrations in the range of from about 10 parts per million to about 1000 parts per million, calculated as free metal in the hydroformylation reaction fluid should be sufficient for most processes, while it is generally preferred to employ from about 10 to 500 parts per million of metal, and more preferably from 25 to 350 parts per million of metal.

In addition to the metal-ligand complex catalyst, free ligand (that is, ligand that is not complexed with the metal) may also be present in the hydroformylation reaction fluid. The free ligand may correspond to any of the aforementioned organophosphorus ligands. The hydroformylation process of this invention may involve from about 0.1 moles or less to about 100 moles or higher, of free ligand per mole of metal in the hydroformylation reaction fluid. Preferably the hydroformylation process of this invention is carried out in the presence of from about 1 to about 50 moles of ligand, and more preferably from about 1.1 to about 4 moles of ligand, per mole of metal present in the reaction fluid; said amounts of ligand being the sum of both the amount of ligand that is bound (complexed) to the metal present and the amount of free (non-complexed) ligand present. If desired, make-up or additional ligand can be supplied to the reaction fluid of the hydroformylation process at any time and in any suitable manner, for example to maintain a predetermined level of free ligand in the reaction fluid.

The substituted or unsubstituted unsaturated olefinic compound that may be employed in the hydroformylation process of this invention includes both optically active (prochiral and chiral) and non-optically active (achiral) olefinic unsaturated compounds containing from 2 to 40, preferably 3 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403, incorporated herein by reference). Moreover, such olefin compounds may further contain one or more ethylenic unsaturated groups, and of course, mixtures of two or more different olefinic unsaturated compounds may be employed if desired. Illustrative mixtures of olefinic starting materials that can be employed in the hydroformylation reactions include, for example, mixed butenes. Further such olefinic unsaturated compounds and the corresponding aldehyde products derived therefrom may also contain one or more groups or substituents that do not unduly adversely affect the hydroformylation process or the process of this invention such as described, for example, in U.S. Pat. Nos. 3,527,809, 4,769,498 and the like, incorporated herein by reference.

Most preferably the subject invention is especially useful for the production of non-optically active aldehydes, by hydroformylating achiral alpha-olefins containing from 2 to 30, preferably 3 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, alkyl alkenoates, for example, methyl pentenoate, alkenyl alkanoates, alkenyl alkyl ethers, alkenols, for example, pentenols, alkenals, for example, pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Illustrative of suitable substituted and unsubstituted olefinic starting materials include those olefinic compounds described in Kirk-Othmer, Encyclopedia of Chemical Technology, Fourth Edition, 1996, the pertinent portions of which are incorporated herein by reference.

The reaction conditions of the hydroformylation process encompassed by this invention may vary over wide ranges. For instance, the $H_2$:CO molar ratio of gaseous hydrogen to carbon monoxide may range from about 1:10 to 100:1 or higher, the more preferred hydrogen to carbon monoxide molar ratio being from about 1:10 to about 10:1. In general, the hydroformylation process may be conducted at a reaction temperature greater than about −25° C., more preferably, greater than about 50° C. The hydroformylation process may be conducted at a reaction temperature less than about 200° C., preferably, less than about 120° C. The target total gas pressure will be selected as described hereinbefore. The minimum total pressure is limited predominately by the amount of carbon monoxide necessary to enter the negative or inverse order region of the rate curve, which will depend upon the specific form of the organophosphorus ligand and hydroformylation catalyst. Generally, the total gas pressure comprising hydrogen, carbon monoxide and olefinic starting compound may range from about 1 psia (6.8% Pa) to about 10,000 psia (68.9 MPa). In general, however, it is preferred that the process be operated at a total gas pressure comprising hydrogen, carbon monoxide and olefin starting compound of less than about 2,000 psia (6,895 kPa) and more preferably less than about 500 psia (34.5 kPa). More specifically the carbon monoxide partial pressure of the hydroformylation process of this invention may vary from about 1 psia (6.8 kPa) to about 1000 psia (6,800 kPa), and more preferably from about 3 psia (20.7 kPa) to about 800 psia (5,516 kPa), and even more preferably, from about 15 psia (103.4 kPa) to about 100 psia (689 kPa); while the hydrogen partial pressure is preferably about 5 psia (34.5 kPa) to about 500 psia (3,450 kPa), and more preferably from about 10 psia (68.0 kPa) to about 300 psia (2,0701 kPa).

The syngas feed flow rate may be any operable flow rate sufficient to obtain the desired hydroformylation process. Typically, the syngas feed flow rate can vary widely and can depend upon the specific form of catalyst, olefin feed flow rate, and other operating conditions. Likewise, the vent flow rate may be any operable vent flow rate sufficient to obtain the desired hydroformylation process. Vent flow rate is typically dependent upon the scale of the reactor and the purity of the reactant and syngas feeds. Suitable syngas feed flow rates and vent flow rates are described in the following reference: "Process Economics Program Report 21D: Oxo Alcohols 21d," SRI Consulting, Menlo Park, Calif., Published December 1999, incorporated herein by reference. Other syngas and vent flow rates may be suitable, depending upon the design of the process as determined by one skilled in the art.

The invention will be further clarified by a consideration of the following examples, which are intended to be purely exemplary of the use of the invention. Other embodiments of the invention will be apparent to those skilled in the art from a consideration of this specification or practice of the invention as disclosed herein.

In the examples that follow, gas flow rates are reported in standard liters per hour (SLH). The hydroformylation reaction rate is reported as the carbon monoxide consumption rate in gram-moles of carbon monoxide consumed per liter of catalyst solution volume per hour (gmole/l/hr). The propylene, carbon monoxide and synthesis gas feed purities were all greater than 99.8%.

EXAMPLE 1

This example illustrates the method of the invention for determining a primary amount of synthesis gas feed flow rate for operation in the inverse carbon monoxide partial pressure region of operation. A reactor was configured as shown in FIG. 3. The reactor was equipped with an impeller (1), impeller shaft (2), propylene feed line and feed flow control (3); syngas feed line and feed flow control (4), the feed line terminating in a sparger in the reactor; vent flow line and vent flow control (5), total pressure sensor (6), exit line for product solution/catalyst to product recovery system (7), and feed line for catalyst returned from product recovery system (8). During the experiment the propylene feed flow rate and reactor vent flow rate were maintained constant within practical limits. To maintain a constant catalyst liquid level and achieve steady-state operation, a portion of the reaction solution was continuously removed from the reactor and passed through a product recovery system to remove a portion of the hydroformylation product and by-products. The treated solution containing catalyst was recovered and recycled back to the reactor on a continuous basis. Synthesis gas was fed through control unit 4 to the reactor, starting at a sub-stoichiometric feed rate relative to the propylene feed rate. The reaction conditions were maintained until steady-state conditions were achieved as indicated by a constant total reactor pressure and constant hydroformylation reaction rate. At steady state conditions, total reactor pressure, hydroformylation reaction rate, vent flow rate and composition, and other reaction conditions were measured. Once completed, the synthesis gas feed rate was adjusted to determine another steady-state data point.

The reactor contained 1 liter of catalyst solution comprising 70 ppm of rhodium and 1.5±0.5 equivalent (based on rhodium) of 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin (Ligand D hereinabove) dissolved in a mixture of butyraldehyde, butyraldehyde dimers, trimers (and higher), along with propylene and propane dissolved in the solution. During the experiment, the propylene feed rate was kept constant at 304 grams/hour. The reactor internal temperature was kept constant at 75° C. The synthesis gas feed ratio $H_2$:CO was kept constant at 1.04. Hence, a reactor vent flow rate of 32.67 SLH, or greater, was sufficient to purge inert components and by-products from the reactor to achieve steady-state operation. The following parameters were measured as a function of synthesis gas feed flow rate: total reactor pressure, CO partial pressure, $H_2$ partial pressure, propylene partial pressure, reactor vent flow rate, and hydroformylation reaction rate, as shown in Table 1.

TABLE 1

| Synthesis Gas Feed Flow Rate, SLH | Total Reactor Pressure, psig | CO Partial Pressure, psia | $H_2$ Partial Pressure, psia | $C_3H_6$ Partial Pressure, psia | Reactor vent flow rate[1], SLH | Hydroformylation rate, gmole/l/hr |
|---|---|---|---|---|---|---|
| 85.34 | 219 | 2.33 | 0.00 | 210.6 | 45.50 | 1.86 |
| 109.50 | 152 | 2.61 | 0.42 | 144.6 | 59.28 | 2.37 |
| 133.65 | 139 | 4.75 | 0.36 | 129.5 | 45.86 | 2.87 |

TABLE 1-continued

| Synthesis Gas Feed Flow Rate, SLH | Total Reactor Pressure, psig | CO Partial Pressure, psia | $H_2$ Partial Pressure, psia | $C_3H_6$ Partial Pressure, psia | Reactor vent flow rate[1], SLH | Hydroformylation rate, gmole/l/hr |
|---|---|---|---|---|---|---|
| 157.80 | 120 | 4.89 | 0.75 | 109.6 | 36.87 | 3.41 |
| 181.96 | 85 | 6.48 | 1.81 | 72.60 | 34.63 | 3.90 |
| 206.11 | 66 | 8.00 | 4.66 | 50.09 | 33.14 | 4.36 |
| 210.94 | 65 | 8.06 | 5.54 | 43.61 | 33.61 | 4.44 |
| 215.77 | 65 | 7.11 | 6.36 | 40.53 | 32.67 | 4.57 |
| 220.60 | 370 | 115.5 | 134.2 | 79.73 | 33.14 | Not at steady state[2] |

[1]Several of the initial reactor vent flow rate data points were higher than the remaining data points; nevertheless, the overall results of the experiment were not adversely affected.
[2]Due to reactant feed pressure limitations, the last data point was not operating under steady-state conditions, and at steady-state the pressure would have been higher than 370 psig. Due to these limitations, the hydroformylation reaction rate could not be measured for these conditions.

The data from Table 1 are plotted in FIG. 2, Total Reactor Pressure versus Synthesis Gas Feed Flow Rate. In FIG. 2 the negative CO order region of the rate curve corresponds to the region of steeply rising total pressure. The final two data points of Table 1 illustrate the reaction system response when the carbon monoxide partial pressure transitions from the positive order region of the rate curve (at 215.77 SLH synthesis gas feed rate with a 7.11 psi carbon monoxide partial pressure) to the negative order region of the rate curve (at 220.60 SLH synthesis gas feed rate with a 115.5 psi carbon monoxide partial pressure). The point is further illustrated in FIG. 2, wherein the total reactor pressure rises sharply on transition from positive to negative order.

Target total pressures were selected from pressures within the steeply rising positive slope) region of FIG. 2 (negative order region of rate curve). For a selected target total pressure in this negative order region, the minimum and maximum primary syngas feed flow rates were selected as the first (1) and second points (2) of intersection, respectively, of the graphed data curve with a straight line drawn parallel to the syngas feed flow axis at the target total pressure. (Note, that some variation may occur in the maximum synthesis gas feed flow (2) depending upon the slope of the line, as determined by the last data point which typically may not be at steady state.) For this example and with reference to Table 1, it was concluded that to operate at a total reactor pressure, for example, of 120 psig in the inverse carbon monoxide partial pressure region, the minimum synthesis gas feed flow rate should be set higher than 157.80 SLH, but less than 215.77 SLH. Accordingly, in the following examples a synthesis gas primary feed flow rate was chosen to be 202 SLH. For reference in subsequent examples, note that a carbon monoxide partial pressure in the range of 15 to 35 psig (103 to 241 kPa) lies in the negative or inverse response region of the rate curve.

EXAMPLE 2

Example 2 illustrates stable operation of a hydroformylation process in the negative order region of the hydroformylation rate curve in accordance with the invention. The reactor was configured as shown in FIG. 4, which was identical to the reactor configuration of FIG. 3 with the exception that the syngas feed flow control comprised primary (4) and secondary (9) flow control valves. Operating parameters were controlled in a manner similar to Example 1. A primary amount of synthesis gas was fed to the reactor through the primary synthesis gas flow rate controller (4). In response to deviations of the measured total pressure from the target pressure of 120 psig (827 kPa), an additional amount of synthesis gas was fed through the secondary forward pressure regulator (9) to adjust the total reactor pressure to the target pressure. The reaction conditions were maintained until steady-state conditions were achieved as indicated by a constant total reactor pressure and constant hydroformylation reaction rate. The total reactor pressure, hydroformylation reaction rate, vent flow rate and composition, and other reaction conditions were then determined. Steady-state operating conditions were demonstrated for more than 10 hours of operation as summarized below.

Figure 5:
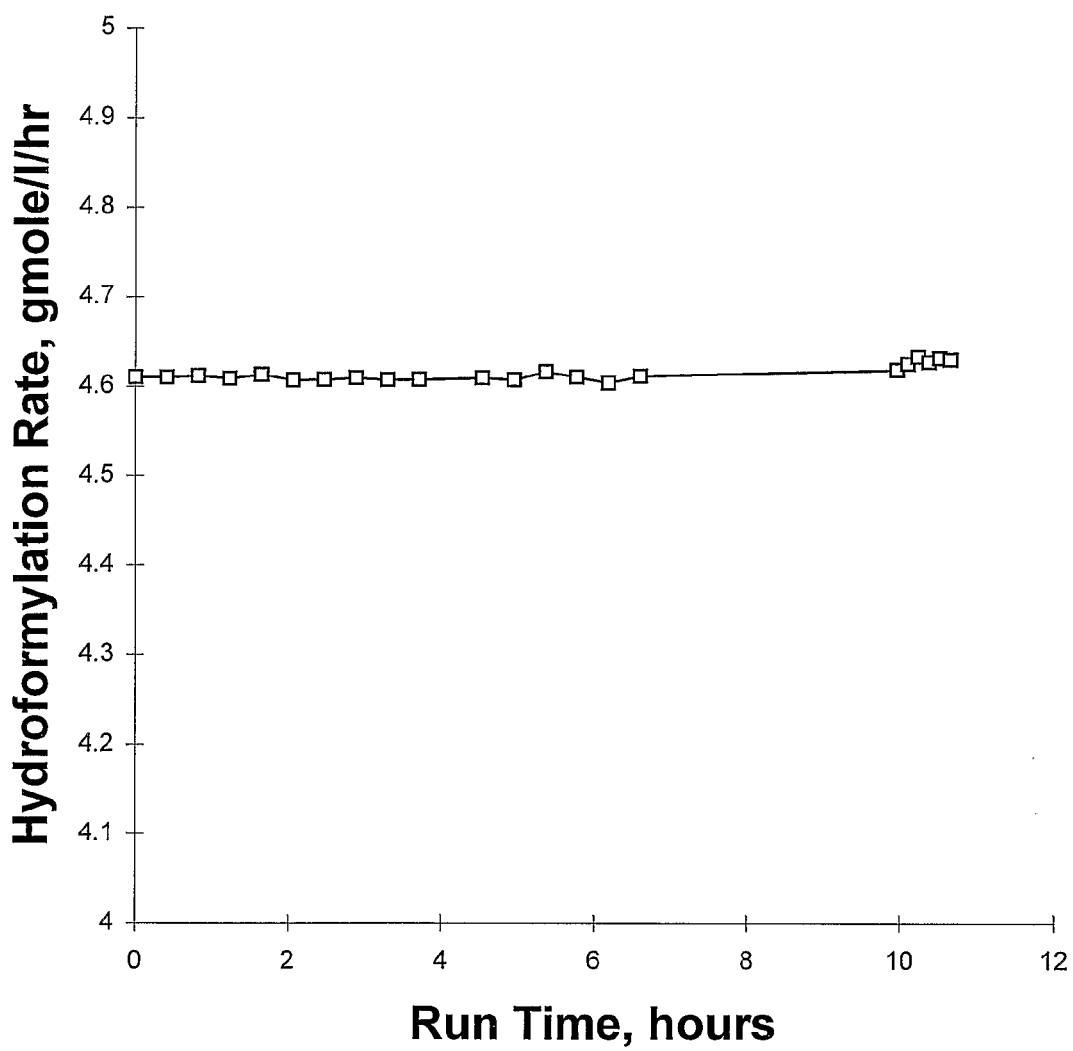
FIG. 5 illustrates a graph of Hydroformylation Reaction Rate versus Run Time for a hydroformylation run in a reactor configured as in FIG. 4.
Figure 6:
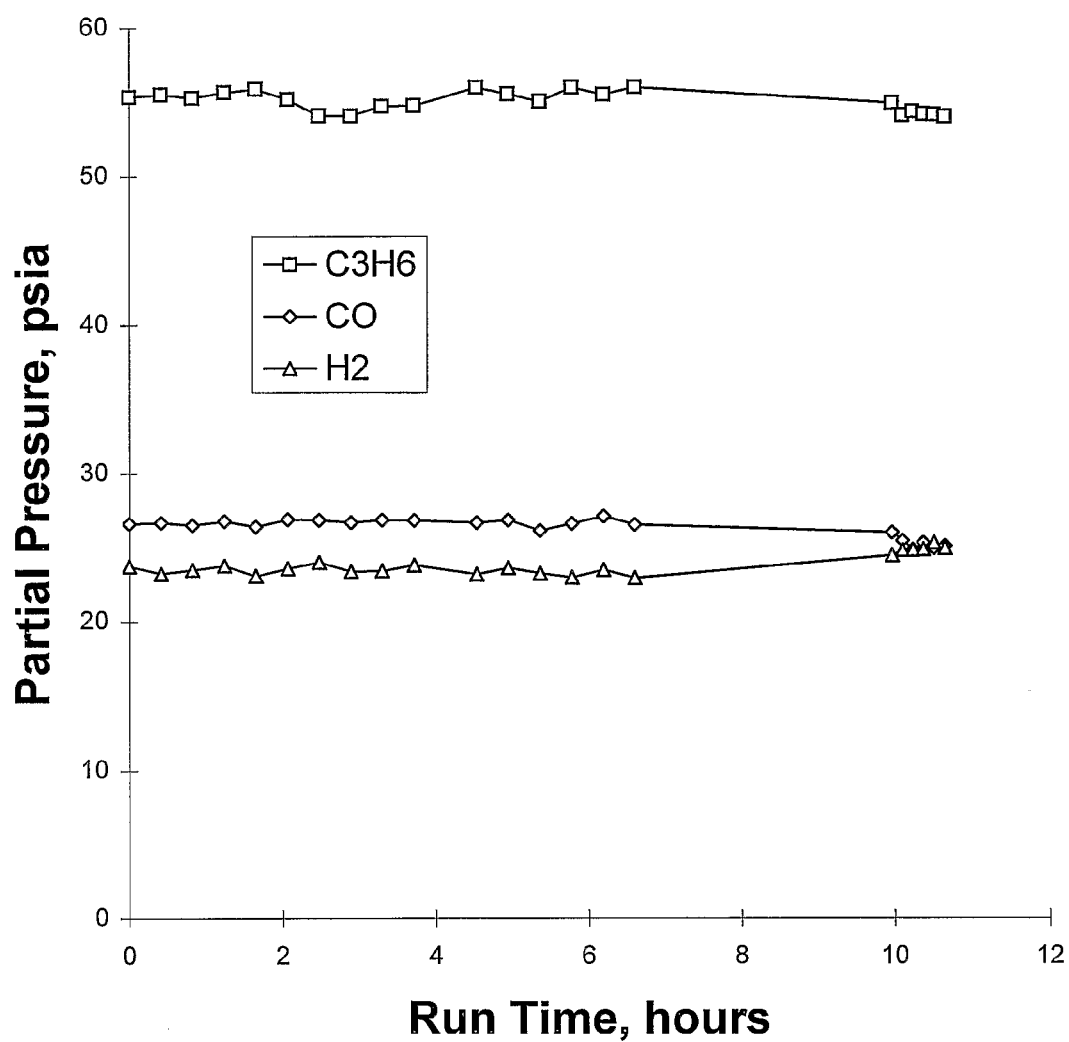
FIG. 6 illustrates a graph of Partial Pressures versus Run Time for a hydroformylation run in a reactor configured as in FIG. 4.

The reaction was conducted under the following process conditions: propylene feed, 299 grams/hour; catalyst temperature, 75° C.; syngas feed ratio ($H_2$:CO), 1.06; syngas primary feed flow rate, 202 SLH; total reactor pressure, 120 psig (827 kPa) (using the synthesis gas feed pressure regulator (9)); and reactor vent flow rate, 38 SLH. During the experiment, the average synthesis gas feed flow rate through the secondary synthesis gas feed pressure regulator (9) was determined to be 27 SLH. The average total syngas feed rate to the reactor included the primary flow rate of 202 SLH plus the average secondary flow rate through the forward pressure regulator of 27 SLH for a total of 229 SLH. Data were graphed as shown in FIG. 5 (Hydroformylation Reaction Rate v. Run Time) and FIG. 6 (Partial Pressures v. Run Time). It is seen in FIGS. 5 and 6 that a steady operation in the negative order region of the rate curve was achieved through the run time of 10.8 hours.

COMPARATIVE EXPERIMENT 1

Figure 7:
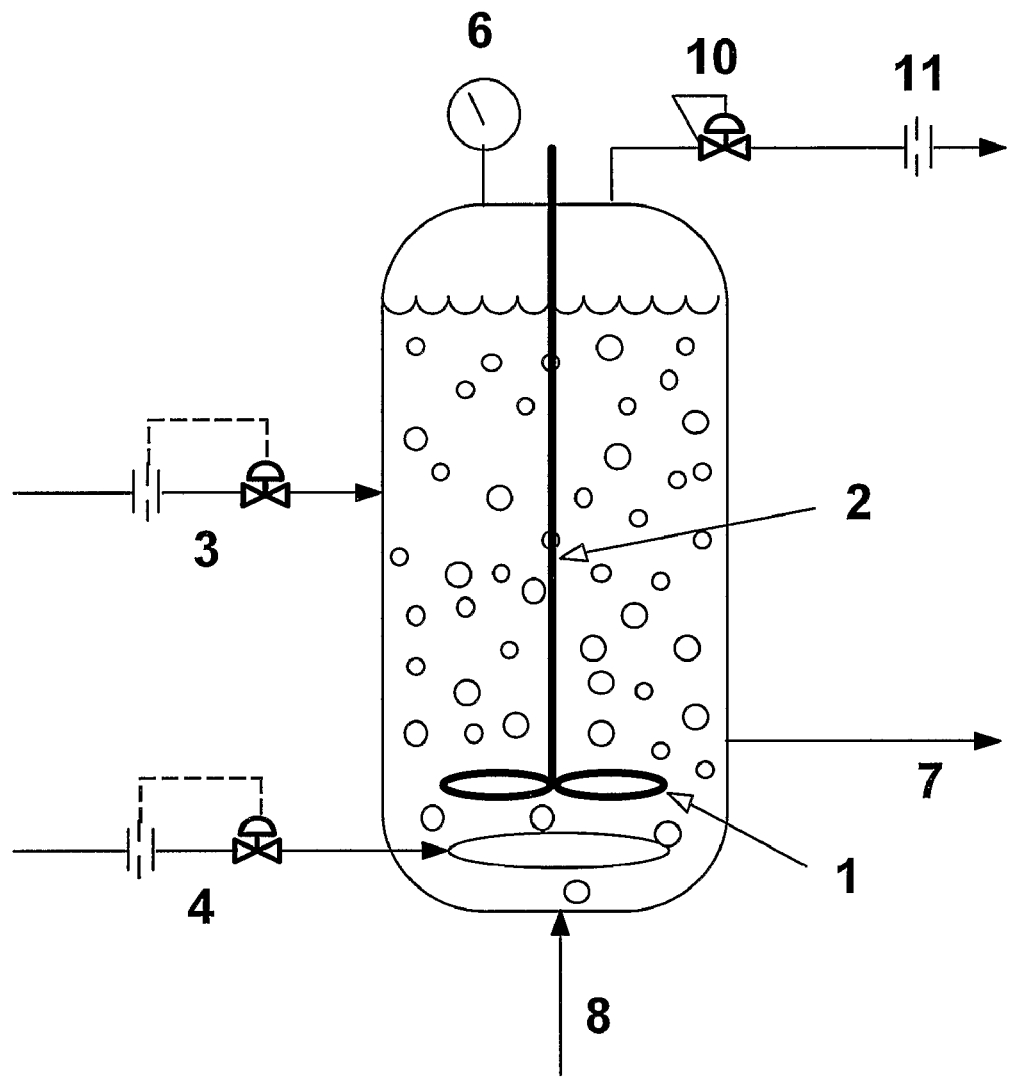
FIG. 7 illustrates a conventional continuous hydroformylation reactor with olefin and syngas feed flow controls, and for comparative purposes versus the reactor of FIG. 4, control of total reactor pressure at the vent flow line.

Comparative Experiment 1 shows that stable operation cannot be maintained by controlling total reactor pressure through the vent line and vent control sensor. After demonstrating stable operation for a total of 10.8 hours as described in Example 2, the reactor was rapidly reconfigured (<1 minute while operating) as shown in FIG. 7. All features were identical to those shown in FIG. 3 including only one syngas feed flow control (4), with the exception that reactor pressure was controlled using a back-pressure regulator in the vent line (10) rather than controlling reactor pressure with incremental syngas feed flow. The reactor vent flow rate was measured (but not controlled) using a vent flow rate sensor (11). Reaction conditions were similar to Example 2 with propylene feed rate, 299 grams/hour; internal catalyst temperature, 75° C.; syngas feed ratio ($H_2$:CO), 1.06 with an initial total feed flow rate of 232 SLH; reactor pressure, 120 psig using the reactor vent back pressure regulator. Results are presented in FIG. 8 (Hydroformylation Reaction Rate v. Run Time) and FIG. 9 (Reactor Vent Flow Rate v. Run Time).

Figure 8:
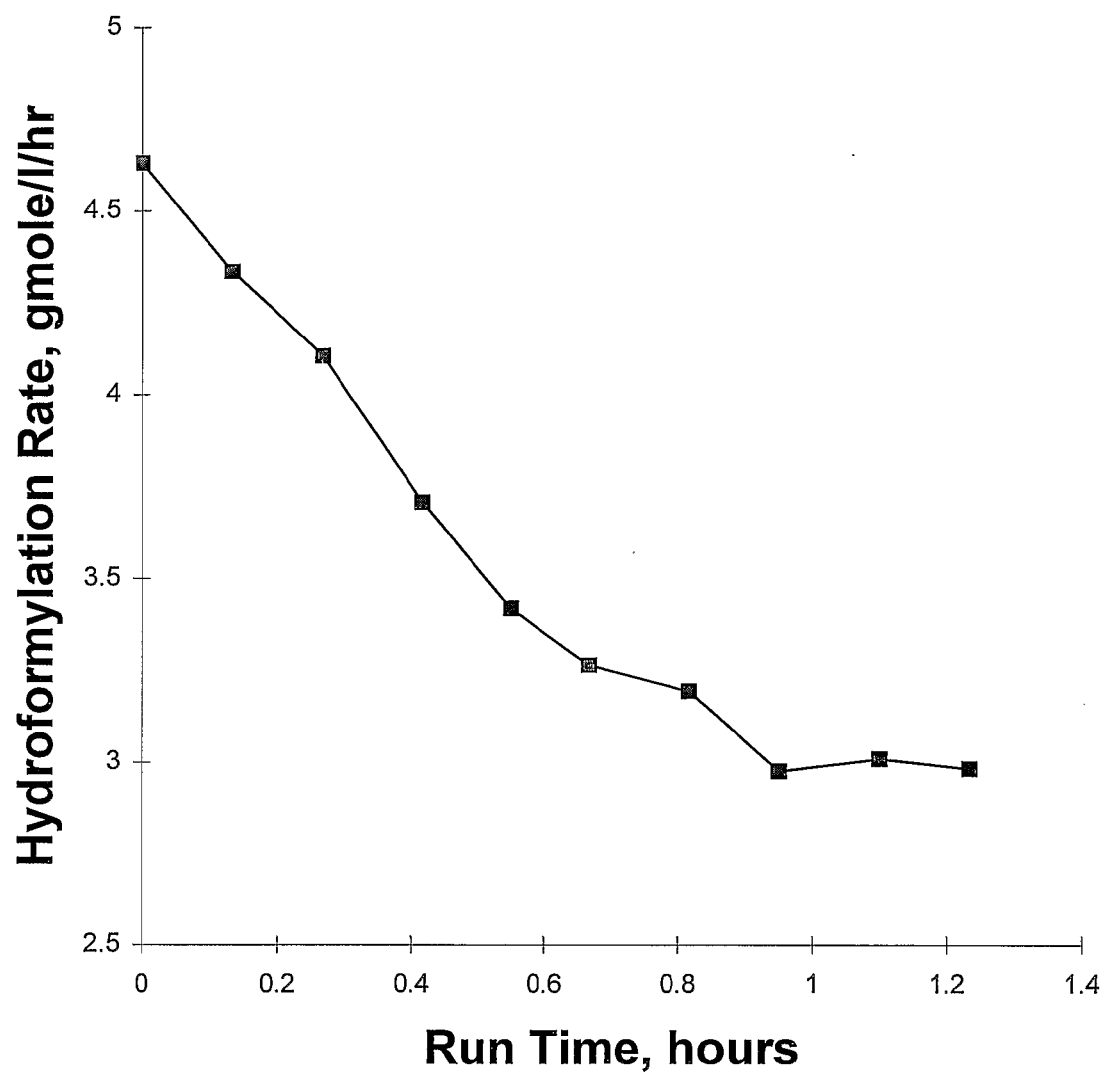
FIG. 8 illustrates a graph of Hydroformylation Reaction Rate versus Run Time for a hydroformylation run in a reactor configured as in FIG. 7.
Figure 9:
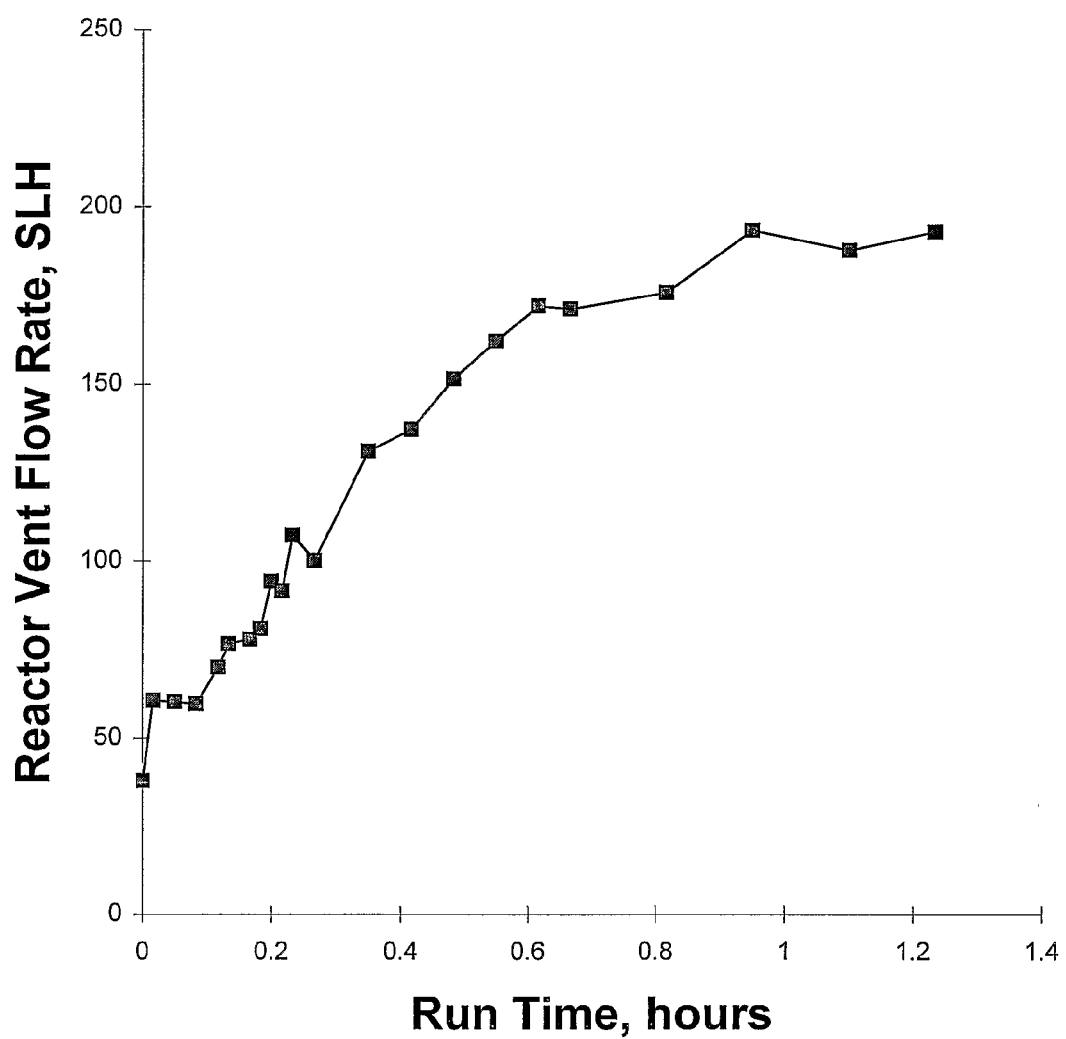
FIG. 9 illustrates a graph of Vent Flow Rate versus Run Time for a hydroformylation run in a reactor configured as in FIG. 7.

As seen from FIGS. 8 and 9, even when starting with stable reactor operation in the inverse carbon monoxide response region of the rate curve, changing the method of reactor pressure control and synthesis gas feed flow rate control from the invention design of Example 2 (FIG. 4) to a conventional design (FIG. 7) resulted in a rapid, uncontrollable change in reaction conditions, including lower reaction rate, higher vent flow rate, and consequentially, higher carbon monoxide and hydrogen partial pressures.

Figure 10:
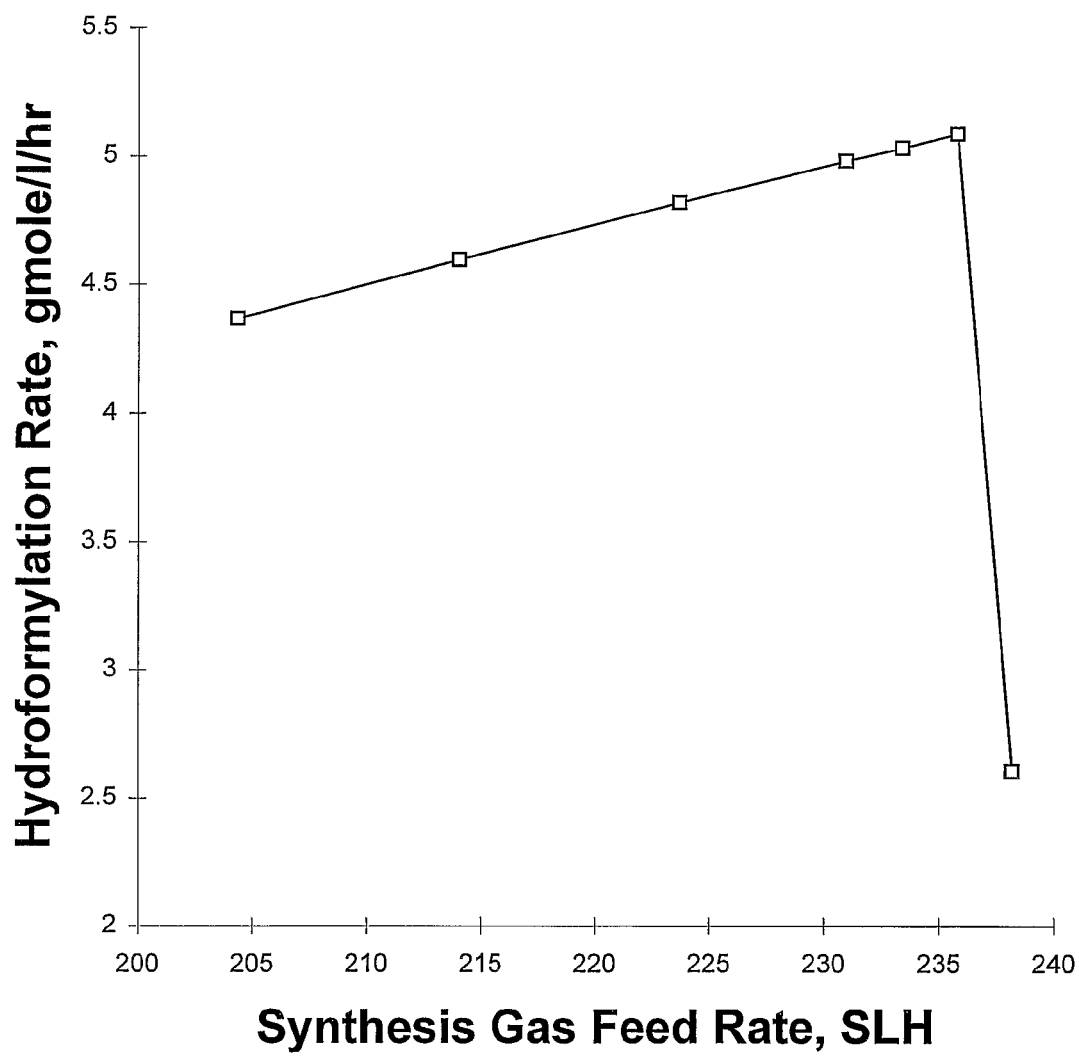
FIG. 10 illustrates a graph of Hydroformylation Reaction Rate versus Synthesis Gas Feed Flow Rate for a hydroformylation run in a reactor configured as in FIG. 7.

Thereafter at 1.25 hours, the synthesis gas feed rate was decreased to 180 SLH, which rapidly resulted in a decrease in the reactor vent flow rate from 193 SLH to 10 SLH at 1.38 hours. At these operating conditions the reaction transitioned back into the positive order region of the hydroformylation rate curve, as previously illustrated in FIG. 2. With reference to FIG. 10, at 1.42 hours the synthesis gas feed rate was increased to 204 SLH, and steady state operating parameters were observed. With increasing carbon monoxide partial pressure, the system became unstable again when the synthesis gas feed rate reached about 238 SLH and the carbon monoxide partial pressure approached the negative side of the hydroformylation rate curve. FIG. 10 (Hydroformylation Rate v. Syngas Feed Flow Rate) illustrates that as the system transitioned from positive order to negative order, the reactor response became unstable again (hours 7.85 through 9.35 of run) as the hydroformylation reaction rate plunged from 4.7 gmole/l/h to 2.4 gmole/l/h. Similar instability, not illustrated in graphical form, was seen in the partial pressures of carbon monoxide, propylene, and hydrogen, and in the reactor vent flow rate. The experiment illustrates again that when approaching the negative response region, a small adjustment in synthesis gas feed flow rate (<1%) can result in large and uncontrollable changes in operating parameters.

EXAMPLE 3

Figure 11:
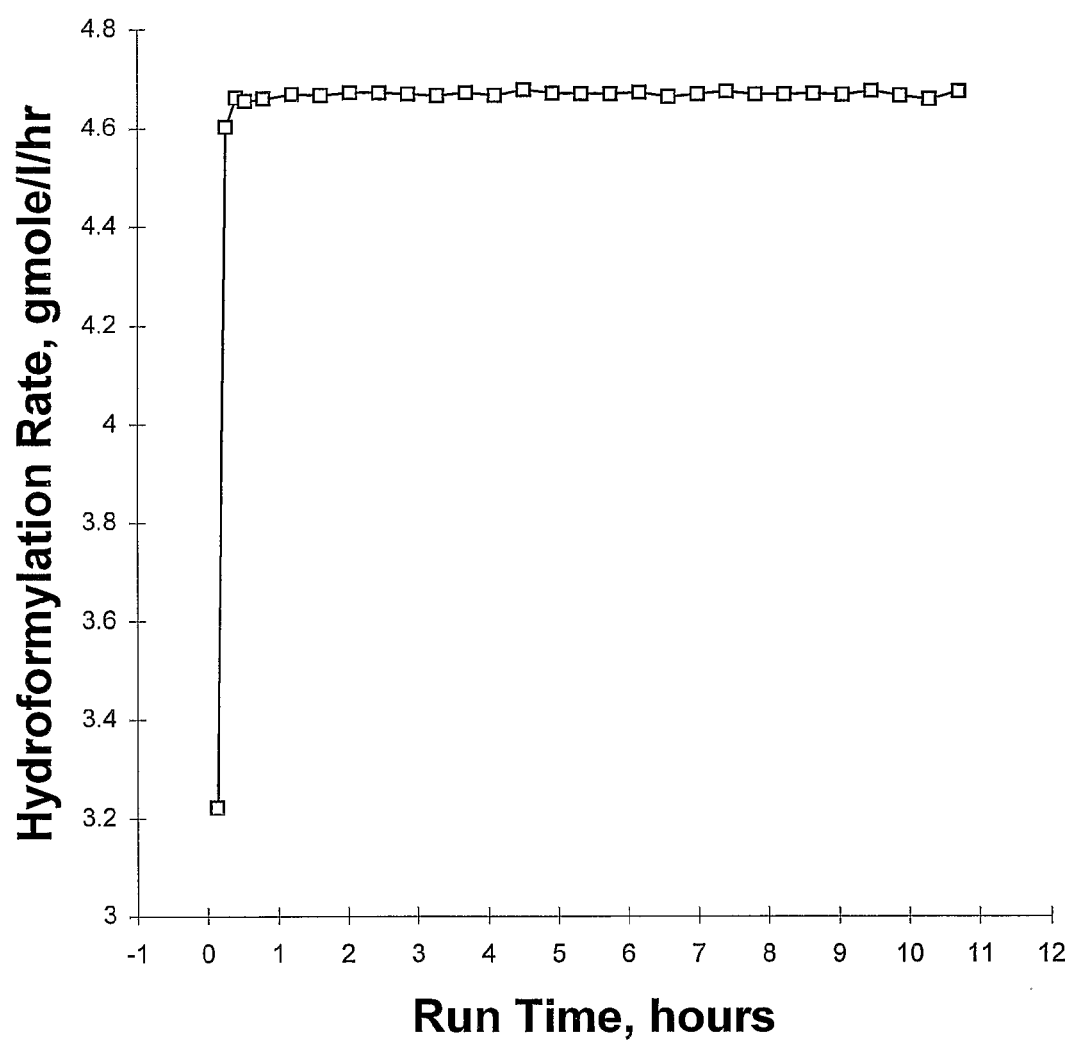
FIG. 11 illustrates a graph of Hydroformylation Reaction Rate versus Run Time for a hydroformylation run in a reactor re-configured as in FIG. 4 in accordance with the invention.
Figure 12:
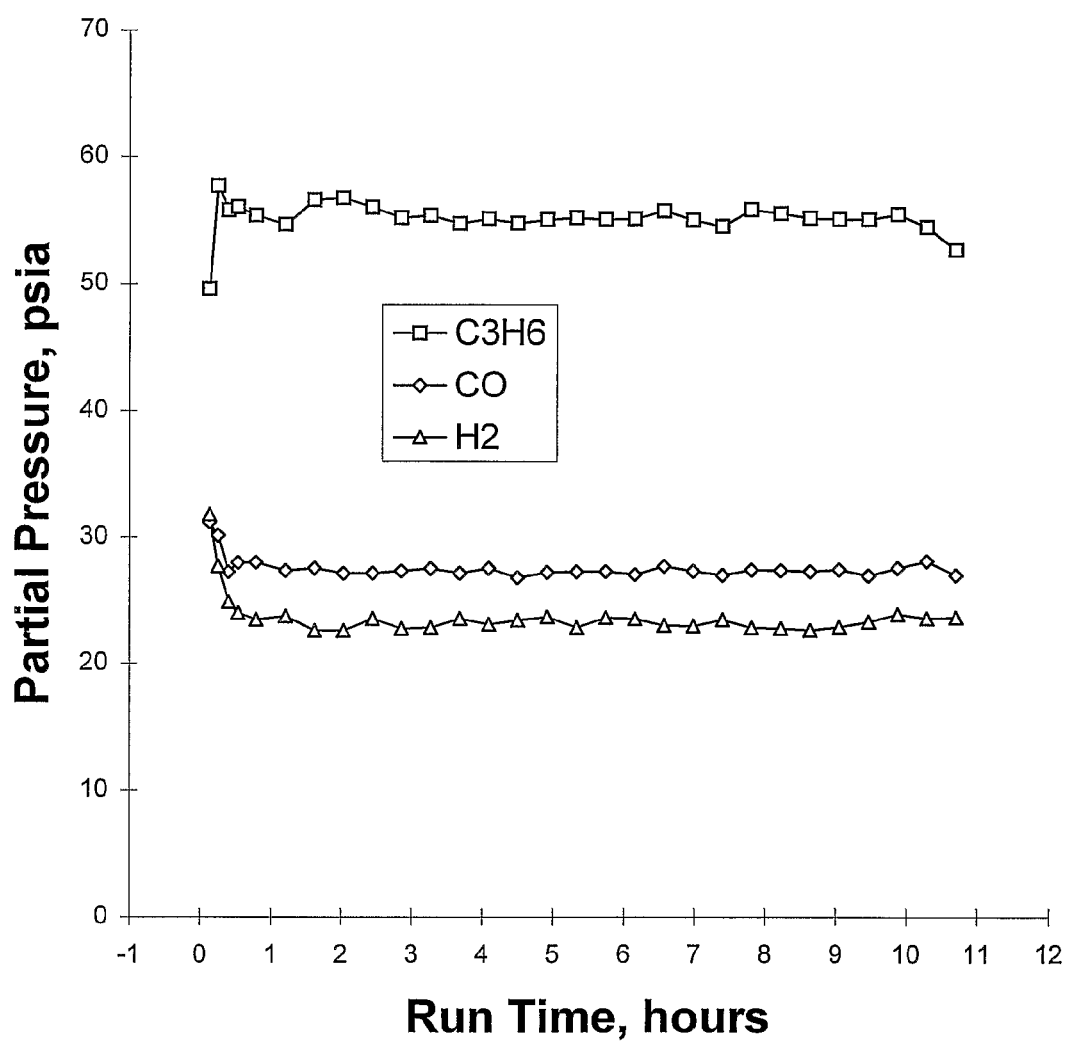
FIG. 12 illustrates a graph of Partial Pressures versus Run Time for a hydroformylation run in a reactor re-configured as in FIG. 4 in accordance with the invention.

This example illustrates how to bring stable operation to the reaction system of Comparative Experiment 1. From the final conditions described in Comparative Experiment 1, the total synthesis gas feed rate was decreased to 180 SLH, and the time clock was set back to 0, Subsequently, at 0.20 hours of operation the total reactor vent flow rate had decreased below 17 SLH, and at that point the reactor was rapidly reconfigured (<1 minute while operating) back to the design shown in FIG. 4. The primary synthesis gas feed rate was reset to 202 SLH (the same flow rate of Example 2). The target total pressure was set at 120 psig (834 kPa), and any deviation of the actual reactor pressure from the target pressure was adjusted via the secondary syngas feed control (FIG. 4, part 9). Without any further changes, the reaction system quickly reestablished the desired stable operating conditions similar to those in Example 2. The following operating conditions were maintained: propylene feed rate, 299 grams/hour; internal catalyst temperature, 75° C.; syngas feed ratio ($H_2$:CO), 1.06 with a primary feed flow rate of 202 SLH; total reactor pressure, 120 psig (using the synthesis gas feed pressure regulator); and reactor vent flow rate, 44 SLH. The reactor vent flow rate of 44 SLH was sufficient to purge inert components and by-products from the reactor to achieve steady-state operation. Results are set forth in FIG. 11 (Hydroformylation Reaction Rate v. Run Time) and FIG. 12 (Partial Pressures v. Run Time), which illustrate stability in hydroformylation reaction rate and reactor partial pressures. Although not illustrated, similar stability was observed in the reactor vent flow rate as a function of time. This example illustrates that stable operation in the desirable negative order region of the hydroformylation rate curve was quickly reestablished by reconfiguring the reaction system to the design specifications of the invention.

EXAMPLE 4

Example 4 illustrates stable operation of a hydroformylation process in the negative order region of the rate curve by use of a secondary pure carbon monoxide feed. The reactor was configured as shown in FIG. 13, which has the same components as the reactor of FIG. 4, with the exception that the synthesis gas feed flow control comprises a primary control valve (4) while the secondary control comprises a pure carbon monoxide feed flow control (12). Operating parameters were otherwise the same as in Example 2. A primary amount of synthesis gas was fed to the reactor through the primary synthesis gas flow rate controller. In response to deviations of the measured total pressure from the target pressure of 113 psig (880 kPa), an amount of carbon monoxide was fed through the secondary forward pressure regulator to adjust the total reactor pressure to the target pressure. The reaction conditions were maintained until steady-state conditions were achieved as indicated by a constant total reactor pressure and constant hydroformylation reaction rate. The total reactor pressure, hydroformylation reaction rate, vent flow rate and composition, and other reaction conditions were then determined. Steady-state operating conditions were demonstrated for more than 12 hours of operation.

Figure 14:
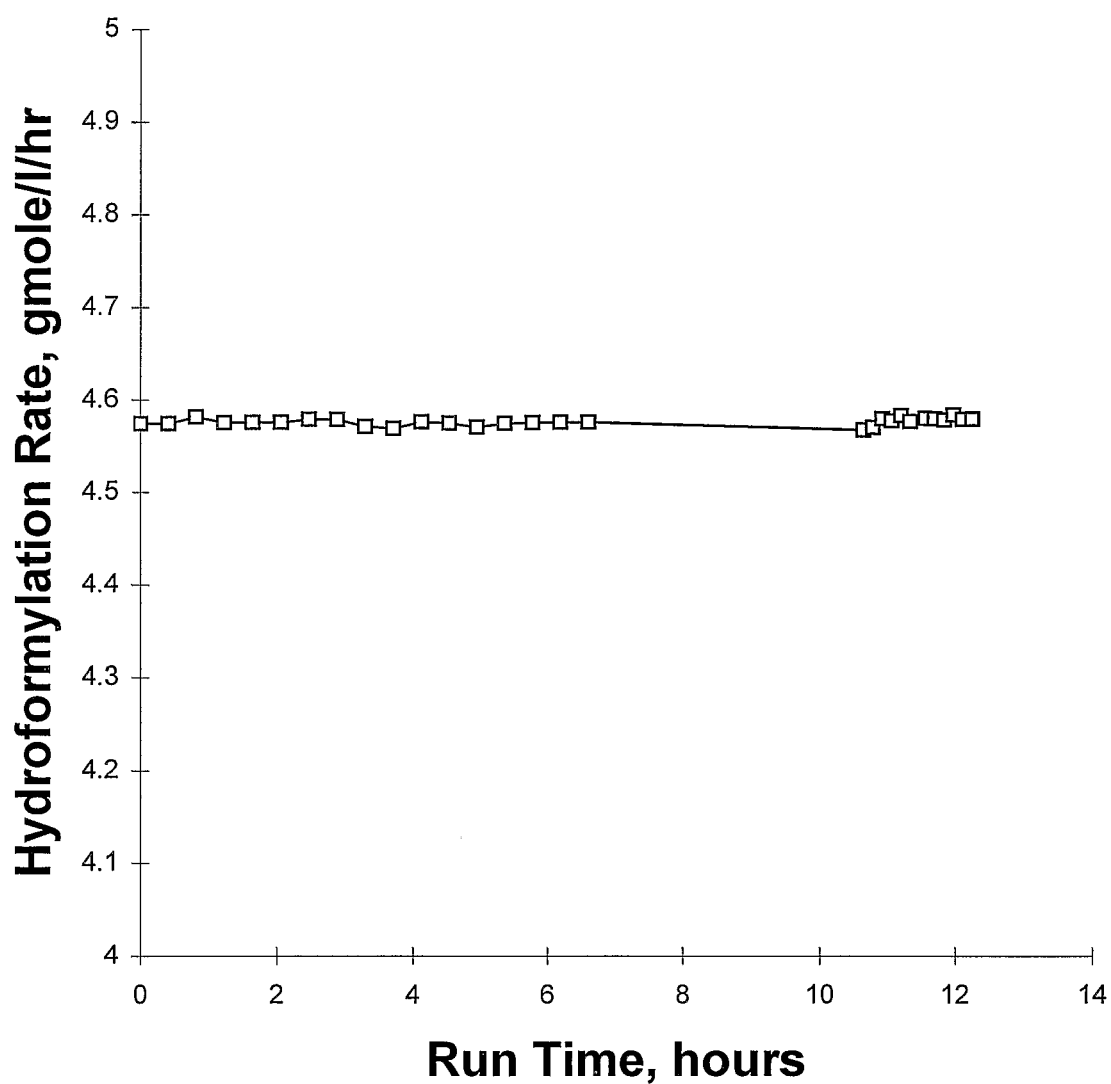
FIG. 14 illustrates a graph of Hydroformylation Reaction Rate versus Run Time for a hydroformylation run in a reactor configured as in FIG. 13.
Figure 15:
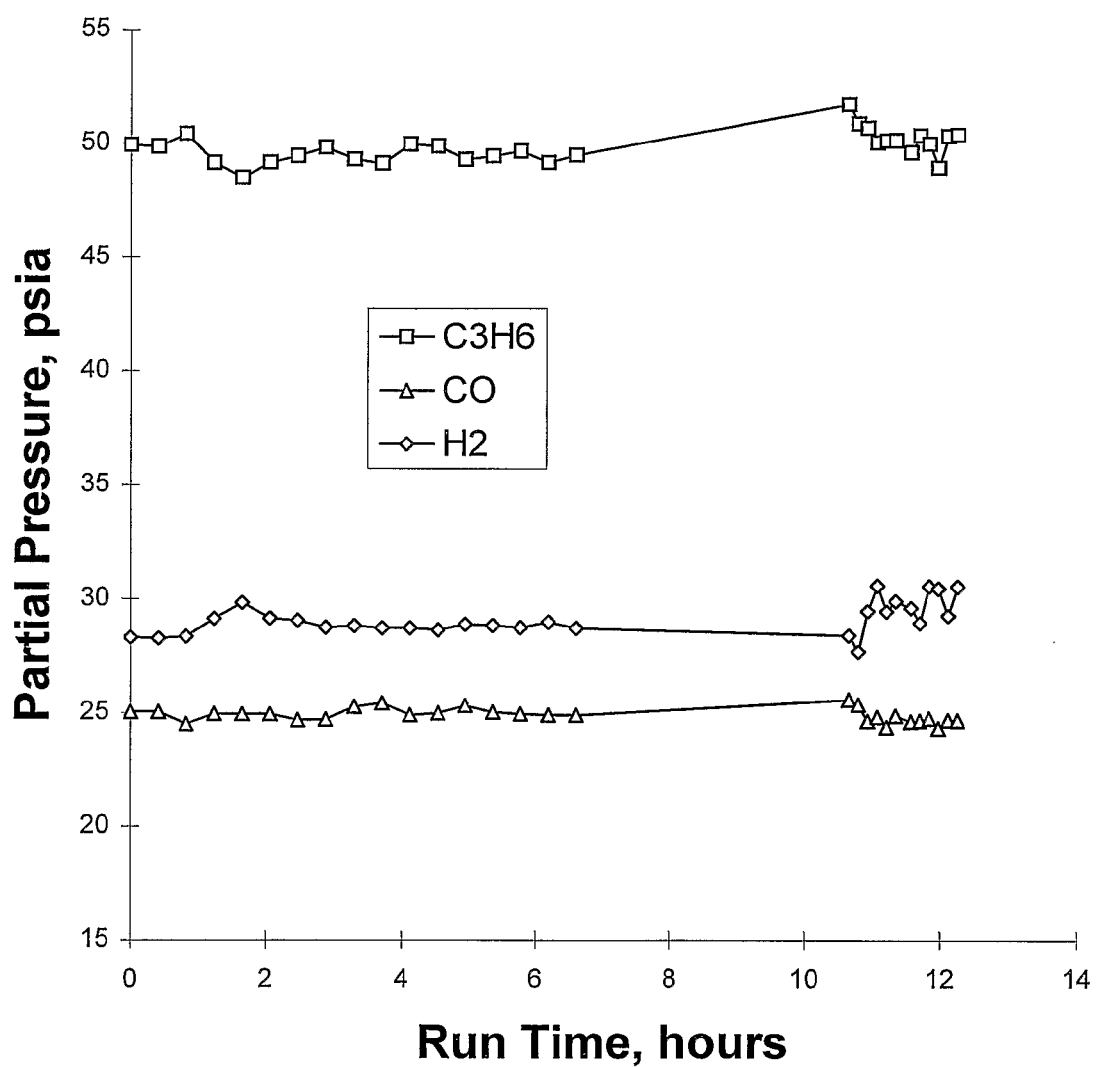
FIG. 15 illustrates a graph of Partial Pressures versus Run Time for a hydroformylation run in a reactor configured as in FIG. 13.

The reaction was conducted under the following process conditions: propylene feed flow rate, 327 grams/hour; catalyst temperature, 75° C.; syngas feed ratio ($H_2$:CO), 1.23; syngas primary feed flow rate, 213 SLH; total reactor pressure, 113 psig (880 kPa) (using the carbon monoxide feed pressure regulator (4)); and reactor vent flow rate, 38.5 SLH. As compared with the previous experiment, the primary syngas feed rate was adjusted higher to compensate for a lower carbon monoxide concentration in the primary syngas feed and the requirement to feed a stoichiometric amount of hydrogen to the reactor. Nevertheless, at 213 SLH the primary syngas feed was in a preferred range and close to the maximum obtained from FIG. 2. During the experiment, the average carbon monoxide feed flow rate through the secondary carbon monoxide feed pressure regulator (12) was determined to be 14.7 SLH. Data were collected and graphed as shown in FIG. 14 (Hydroformylation Reaction Rate v. Run Time) and FIG. 15 (Partial Pressure v. Run Time). The graphs illustrate stable reactor operation in the inverse carbon monoxide region of the rate curve by using an operating mode comprising a constant vent flow rate, a constant primary synthesis gas feed rate, and a variable carbon monoxide feed rate to control total reactor pressure.

COMPARATIVE EXPERIMENT 2

Comparative Experiment 2 shows that stable operation cannot be maintained in the inverse region of the rate curve by using a constant primary synthesis gas feed flow rate combined with a constant secondary carbon monoxide feed flow rate. After demonstrating stable operation for a total of 12.25 hours as described in Example 4, the reactor was rapidly reconfigured (<1 minute while operating) as shown in FIG. 16 and the time clock was reset back to zero. All design features were identical to those used in FIG. 13, with the exception that a constant carbon monoxide feed flow control, (4) and (13), was utilized and total reactor pressure was controlled with a back-pressure regulator (10) on the reactor vent line. The reactor vent flow rate was measured (but not controlled) using a vent flow rate sensor (11).

Figure 17:
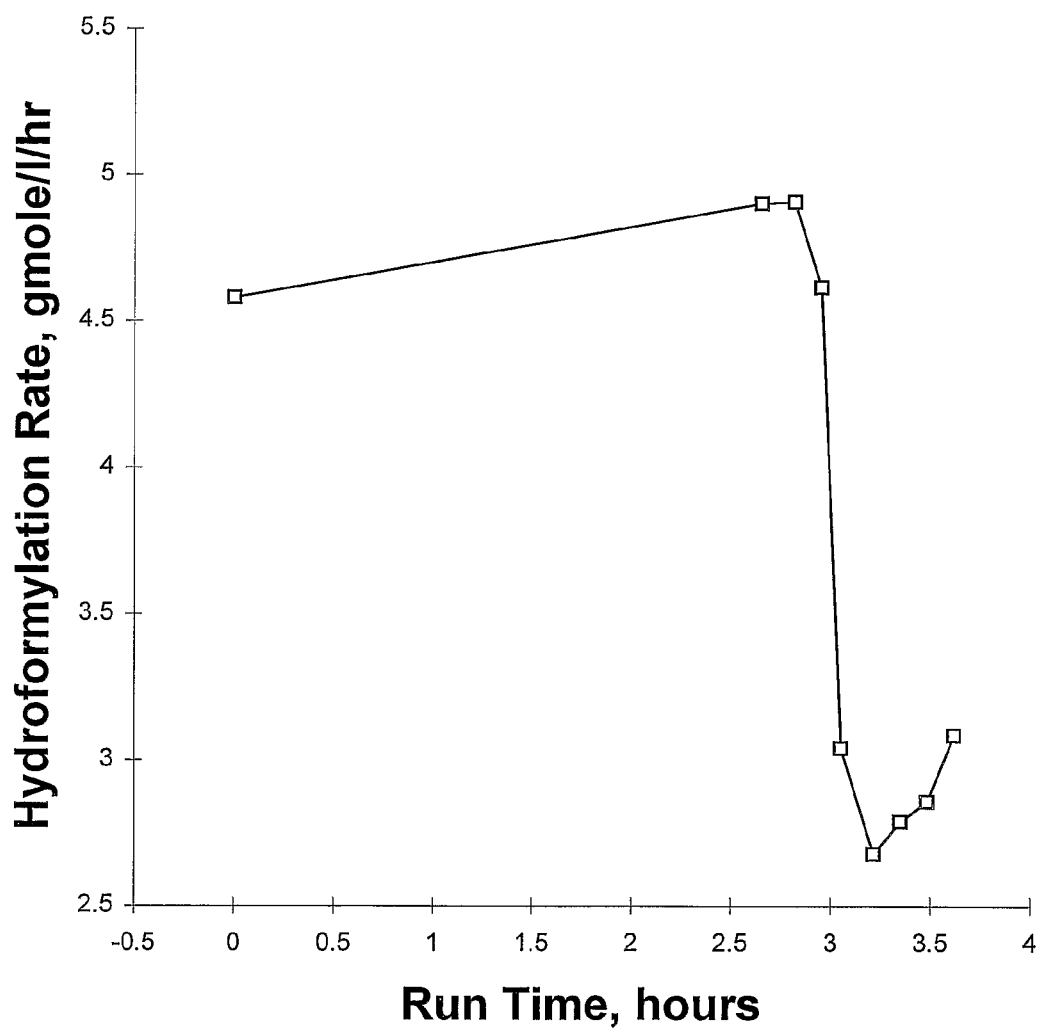
FIG. 17 illustrates a graph of Hydroformylation Reaction Rate versus Run Time for a hydroformylation run in a reactor configured as in FIG. 16.
Figure 18:
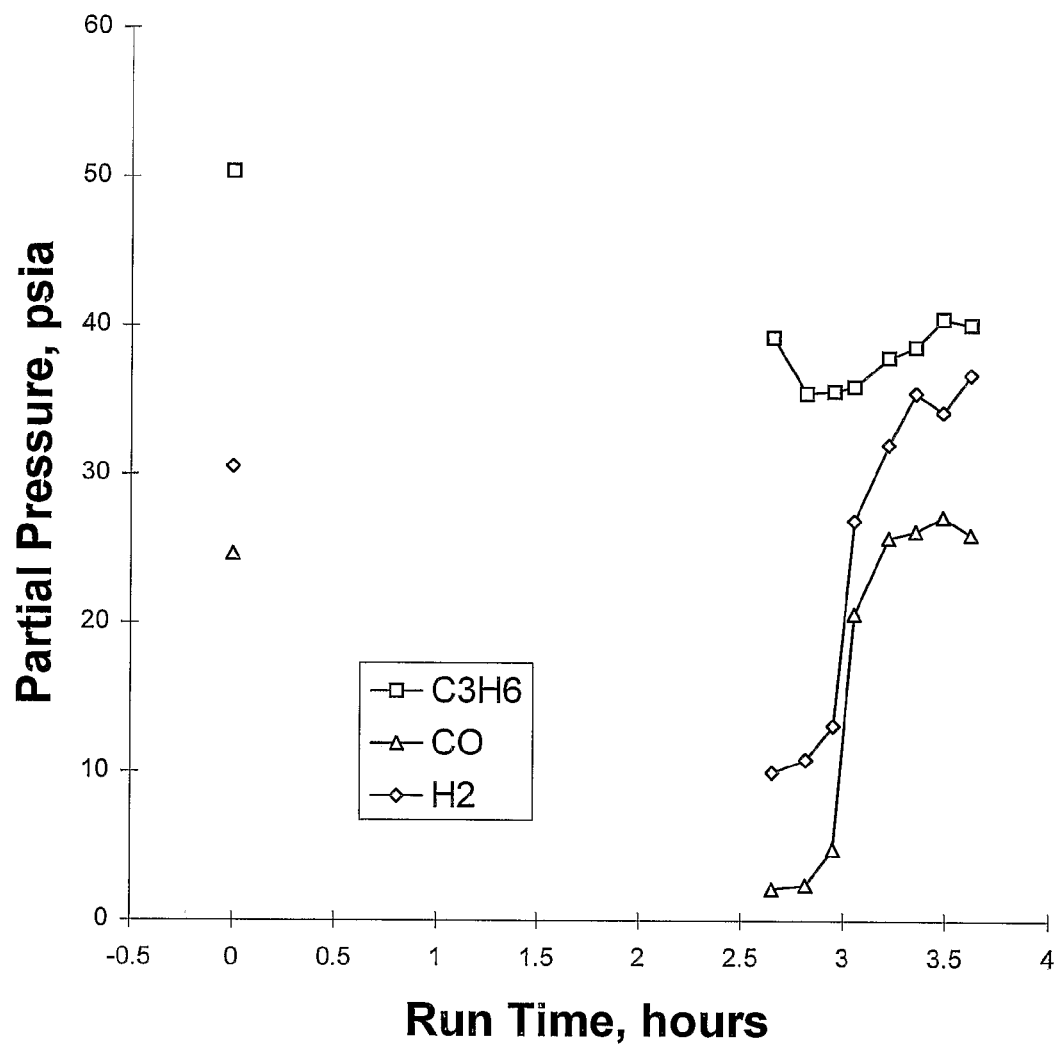
FIG. 18 illustrates a graph of Partial Pressures versus Run Time for a hydroformylation run in a reactor configured as in FIG. 16.

Reaction conditions were similar to Example 4: propylene feed rate, 327 grams/hour; internal catalyst temperature, 75° C.; syngas feed ratio ($H_2$:CO), 1.23 with a constant feed flow rate of 213 SLH; constant carbon monoxide feed flow rate, 14.7 SLH; reactor pressure setting, 109 psig using the reactor vent back pressure regulator (when the reactor pressure was less than the setting, the reactor vent flow rate was zero). Data are presented in FIG. 17 (Hydroformylation Reaction Rate v. Run Time) and FIG. 18 (Partial Pressures v. Run Time).

Initially, the change of pressure control resulted in a rapid, undesirable and uncontrollable drop in total reactor pressure, reaching a minimum of 68 psig at about 0.3 hours of operation. While the reactor was below the set pressure of 109 psig, no vent gas was available for analysis and hence the reactor partial pressures and hydroformylation rate could not be calculated. At 2.65 hours, when some vent flow was reestablished from the reactor, it became apparent that for at least some of the previous operating time the carbon monoxide pressure was about 2 psi or less resulting in operation in the undesirable positive order region of the kinetic curve. At 2.95 hours the reactor vent flow rate rapidly and uncontrollably increased to about 170 SLH. Eventually, this resulted in other undesirable operating conditions, namely, significantly higher carbon monoxide and hydrogen partial pressures, significantly lower hydroformylation reaction rate, and significantly higher reactor vent flow rate. This experiment illustrates that even when starting with stable reactor operation in the inverse carbon monoxide response region of the rate curve, but changing the method of reactor pressure control from the invention design of FIG. 13 to the conventional design of FIG. 16, rapid uncontrollable changes in reaction conditions can occur.

EXAMPLE 5

This example illustrates how to re-establish stability from the unstable conditions of Comparative Experiment 2. The reactor at end of Comparative Experiment 2 was rapidly reconfigured (<1 minute while operating) back to the design shown in FIG. 13; the synthesis gas feed rate was decreased to 97 SLH; the carbon monoxide forward pressure regulator was set to 109 psig; and the time clock was set back to 0, Subsequently, the syngas feed rate was increased in several steps eventually reaching 211 SLH at 0.3 hours of operation. At 0.37 hours the carbon monoxide forward pressure regulator of secondary CO flow control (12) was increased from 109 psig to 113 psig. Without any further changes, the reaction system quickly reestablished the desired stable operating conditions similar to those in Example 4. The following operating conditions were maintained: propylene feed rate, 327 grams/hour; internal catalyst temperature, 75° C.; syngas feed ratio ($H_2$:CO), 1.23 with a primary syngas feed flow rate of 211 SLH; total reactor pressure, 113 psig (880 kPa) (using the synthesis gas feed pressure regulator (12)); and reactor vent flow rate, 41.3 SLH. The reactor vent flow rate of 41.3 SLH was sufficient to purge inert components and by-products from the reactor to achieve steady-state operation for a total of 12 hours.

EXAMPLE 6

This embodiment of the invention is illustrated with the reactor design shown in FIG. 19, wherein the reactor vent flow rate is maintained using a variable synthesis gas feed rate control [(14) combined with (4)] to control the vent flow rate through a back pressure regulator (10) used to maintain the total reactor pressure. Note that component 11 of FIG. 19 is a reactor vent flow sensor. At the start, the catalyst composition, process conditions, and reactor configuration are employed as shown in FIG. 3 and Example 1, to determine the desired reactor target total pressure and primary syngas feed flow rate. The minimum vent flow rate is also determined from the reactant feed purities, the rate being sufficient to purge inert components and by-products from the reactor to achieve steady-state operation. After setting these parameters, the same reaction conditions and reactant feed flow rates are established as in Example 2. During the experiment the propylene feed flow rate (3) and reactor vent flow rate are controlled as constant as practical. To maintain a constant catalyst liquid level and achieve steady-state operation, catalyst solution is continuously removed from the reactor (7) and passed through a product recovery system to remove the hydroformylation product and by-products. The catalyst solution is recovered and recycled back to the reactor on a continuous basis (8). A primary amount of synthesis gas is fed to the reactor through the synthesis gas feed flow rate controller (4). A variable amount of synthesis gas is controlled through a secondary control valve (14) thereby controlling the reactor vent flow rate. The total reactor pressure is controlled with a back pressure regulator on the reactor vent line (10). The reaction conditions are maintained and steady-state conditions are achieved as indicated by a constant total reactor pressure and constant hydroformylation reaction rate.

EXAMPLE 7

This example illustrates obtention of a hydroformylation rate curve as a function of carbon monoxide partial pressure over both positive and negative order regions of the rate curve. Without the method of this invention, difficulties would be encountered in obtaining reaction rates in the negative order region of the rate curve.

Figure 20:
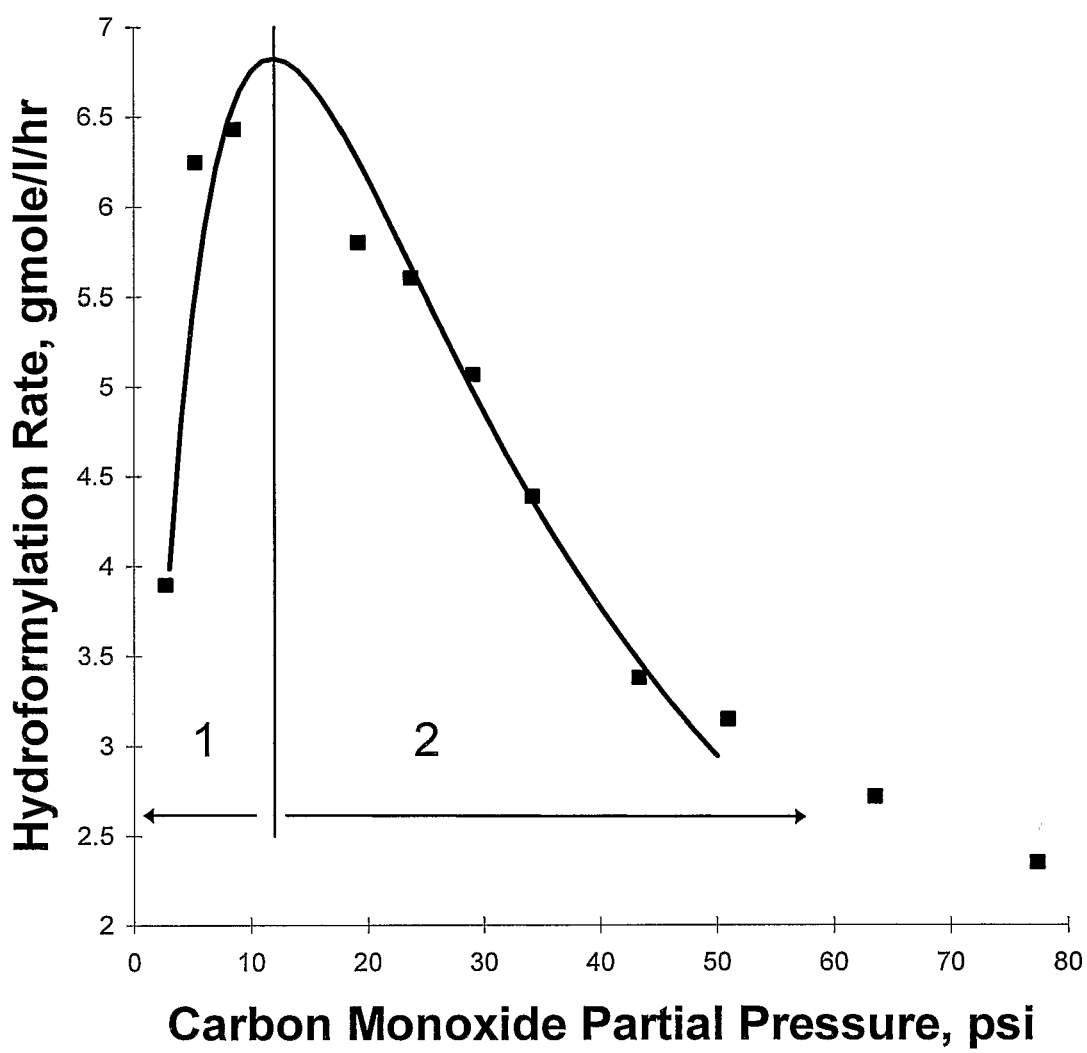
FIG. 20 illustrates a graph of Hydroformylation Reaction Rate versus Carbon Monoxide Partial Pressure for the actual hydroformylation of propylene with carbon monoxide and hydrogen in the presence of a specific metal-organopolyphosphite ligand complex catalyst.

Propylene was hydroformylated using syngas (CO+$H_2$) in the presence of a rhodium catalyst prepared with 1.5±0.5 equivalent (based on rhodium) of 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin (Ligand D hereinabove). Reference is made to FIG. 20. For the first three data points through the positive order region of the rate curve, a conventional reactor (1 liter capacity) was employed having the design of FIG. 7. For the remaining data points in the negative order region of the rate curve, the reactor was configured as shown in FIG. 4, using the process of this invention to stabilize process parameters. The reactor internal temperature was kept constant at 75° C. Process conditions and raw hydroformylation reaction rates (gmole/k/hr) are set forth in Table 2.

TABLE 2[1,2]

| Propylene Feed Flow, | Syngas Feed Flow, | Syngas Ratio, | Reactor Vent Flow, | Reactor Partial Pressures (psia) | | | Total Reactor Pressure, | [Rh] | Raw Reaction Rate, | Adjusted Rate[3] | Product Isomer Mole Ratio | Propane Selectivity (mole |
|---|---|---|---|---|---|---|---|---|---|---|---|---|
| g/h | SLH | $H_2$:CO | SLH | CO | $H_2$ | $C_3H_6$ | psig | ppm | gmole/l/h | gmole/l/h | (N/I) | percent) |
| 245.5 | 181.0 | 1.307 | 32.4 | 2.68 | 25.1 | 50.8 | 120 | 69 | 3.90 | 3.89 | 47.3 | 16.04 |
| 416.3 | 314.4 | 1.186 | 38.4 | 5.25 | 27.7 | 51.8 | 102 | 74 | 6.84 | 6.25 | 47.7 | 8.65 |

TABLE 2[1,2]-continued

| Propylene Feed Flow, | Syngas Feed Flow, | Syngas Ratio, | Reactor Vent Flow, | Reactor Partial Pressures (psia) | | | Total Reactor Pressure, | [Rh] | Raw Reaction Rate, | Adjusted Rate[3] | Product Isomer Mole Ratio | Propane Selectivity (mole |
|---|---|---|---|---|---|---|---|---|---|---|---|---|
| g/h | SLH | $H_2$:CO | SLH | CO | $H_2$ | $C_3H_6$ | psig | ppm | gmole/l/h | gmole/l/h | (N/I) | percent) |
| 345.6 | 284.8 | 1.141 | 37.6 | 8.55 | 25.3 | 48.1 | 95 | 69 | 6.10 | 6.43 | 42.1 | 5.92 |
| 347.9 | 298.7 | 1.068 | 39.1 | 19.2 | 24.2 | 50.8 | 105 | 77 | 6.49 | 5.80 | 34.3 | 2.87 |
| 331.3 | 280.9 | 1.044 | 39.7 | 23.8 | 26.0 | 48.7 | 109 | 79 | 6.16 | 5.60 | 32.7 | 2.66 |
| 296.3 | 253.2 | 1.027 | 39.4 | 29.1 | 26.0 | 49.1 | 114 | 77 | 5.48 | 5.07 | 29.3 | 2.37 |
| 207.2 | 171.4 | 1.014 | 31.5 | 34.2 | 24.8 | 50.7 | 120 | 61 | 3.88 | 4.39 | 26.6 | 2.07 |
| 188.1 | 160.7 | 0.979 | 30.3 | 43.3 | 24.4 | 52.0 | 129 | 71 | 3.56 | 3.38 | 23.4 | 1.55 |
| 169.0 | 145.4 | 0.964 | 32.0 | 51.0 | 26.1 | 49.0 | 135 | 70 | 3.08 | 3.15 | 22.6 | 1.67 |
| 146.2 | 136.7 | 0.908 | 31.0 | 63.5 | 24.5 | 50.2 | 147 | 69 | 2.69 | 2.72 | 19.6 | 1.31 |
| 126.2 | 105.4 | 0.856 | 32.7 | 77.4 | 25.0 | 48.8 | 160 | 70 | 2.29 | 2.35 | 17.7 | 1.22 |

[1]Temperature was 75° C. in all runs. Catalyst volume was 1 liter in all runs.
[2]The data were typically collected at high syngas conversions; thus, normal variations and experimental errors in collecting the data may result in conversions for CO and/or $H_2$, if calculated, which are higher than 100 percent, but not higher than about 110 percent.
[3]Adjusted Rate - Adjusts the reaction rate to 50 psi propylene partial pressure and 70 ppm rhodium concentration using first order kinetic responses for both variables.
[4]Product isomer ratio (N/I) refers to the molar ratio of normal to branched aldehyde products, as measured in the reactor vent gas.
[5]Propane selectivity is calculated as 100x the moles of propane produced divided by the total moles of propylene reacted to form butyraldehyde and propane.

Since each data point in Table 2 varied slightly in propylene partial pressure and rhodium concentration, the raw hydroformylation rates were adjusted to a standardized propylene partial pressure of 50 psi (345 kPa) and a rhodium concentration of 70 parts per million (ppm). The adjusted rates are also set forth in Table 2.

The adjusted hydroformylation reaction rates were plotted as a function of CO partial pressure as shown in FIG. 20, confirming the theoretical graph presented in FIG. 1. The data provide a means of selecting CO partial pressures close to the maximum reaction rate in the negative order region of the rate curve, beneficially, such that reaction rate and product isomer ratio are maximized and alkane formation is minimized. In like manner, similar plots and CO partial pressure ranges can be obtained for any ligand selected for use, thereby providing the operational parameters resulting in maximum rate and maximum normal/branched isomer ratios at minimum alkane formation.

The invention claimed is:

1. A hydroformylation process comprising reacting one or more reactants, carbon monoxide, and hydrogen in the presence of a hydroformylation catalyst to produce a reaction product fluid comprising one or more products, wherein said process is conducted at a carbon monoxide partial pressure such that reaction rate increases as carbon monoxide partial pressure decreases and the reaction rate decreases as carbon monoxide partial pressure increases; and wherein the following process steps are conducted to stabilize reaction rate, total pressure, vent flow rate, reaction temperature, or a combination thereof; the process steps comprising at least one of the following process control schemes selected from:

Scheme A:
(a1) establishing a target total pressure;
(a2) detecting the total pressure and determining the difference between the detected total pressure and the target total pressure; and
(a3) based on the pressure difference measured in step (a2), manipulating a feed flow of gas comprising carbon monoxide to adjust the detected total pressure essentially to the target total pressure; and Scheme B:
(b1) establishing a target vent flow rate;
(b2) detecting the vent flow rate and determining the difference between the detected vent flow rate and the target vent flow rate; and
(b3) based on the vent flow rate difference measured in step (b2), manipulating a feed flow rate of gas comprising carbon monoxide to adjust the detected vent flow rate essentially to the target vent flow rate.

2. The process of claim 1 wherein process steps (a1) through (a3) and process steps (b1) through (b3) are all implemented so as to adjust the detected total pressure to the target total pressure and to adjust the detected vent flow rate to the target vent flow rate.

3. The process of claim 1 wherein one or more olefinic unsaturated compounds are contacted with carbon monoxide and hydrogen to prepare one or more aldehydes.

4. The process of claim 3 wherein the olefinic unsaturated compound comprises from 3 to 20 carbon atoms.

5. The process of claim 1 wherein the hydroformylation catalyst comprises a metal-organophosphorus ligand complex catalyst.

6. The process of claim 5 wherein the hydroformylation catalyst comprises a metal-organopolyphosphite ligand complex catalyst.

7. The process of claim 6 wherein the hydroformylation catalyst comprises a rhodium-organopolyphosphite ligand complex catalyst.

8. The process of claim 1 wherein the target total pressure is selected from a range of pressures in a region of steepest positive slope of a graph of Total Pressure versus Synthesis Gas Feed Flow Rate.

9. The process of claim 1 wherein a minimum target vent flow rate is selected as the vent flow rate equal to the input stoichiometric excess of hydrogen and inerts.

10. The process of claim 1 wherein a primary source of carbon monoxide is provided to the process to satisfy essentially the stoichiometric requirements of the hydroformylation process, and the detected total pressure is adjusted to the target total pressure by means of a secondary source of a carbon monoxide-containing gas.

11. The process of claim 10 wherein the primary source of carbon monoxide comprises a primary feed of syngas to the reactor; and optionally, wherein the secondary source of carbon monoxide-containing gas comprises a syngas feed or a pure carbon monoxide feed, or a feed comprising carbon monoxide and an inert gas.

12. The process of claim 1 wherein the total pressure is controlled by adjusting the flow rate of a carbon monoxide-containing inlet gas, while the vent flow rate of discharged gas from the reactor is maintained at a constant flow rate.

13. The process of claim 1 wherein the vent flow rate of a discharged gas from the reactor is controlled by adjusting the flow rate of a carbon monoxide-containing gas fed to the reactor, while maintaining the target total pressure.

14. The process of claim 1 wherein the hydroformylation process is conducted in a plurality of continuous stirred tank reactors connected in series, wherein the total pressure is detected by a detection means located on one or more of the reactors in series, and a signal is transmitted to a carbon monoxide inlet line to one or more of the reactors in series, so as to adjust the total pressure over the plurality of reactors to the target pressure.

15. The process of claim 1 wherein the hydroformylation process is conducted in a plurality of continuous stirred tank reactors connected in series, wherein the vent flow rate is detected by a detection means located in a vent line from one or more of the reactors in series, and a signal is transmitted to a carbon monoxide inlet line to one or more of the reactors in series, so as to adjust the vent flow rate over the plurality of reactors to the target vent flow rate.

16. The process of claim 1 wherein the hydroformylation process is conducted in a plurality of continuous stirred tank reactors connected in series, wherein the total pressure is detected by a detection means located on one or more of the reactors in series, and a signal is transmitted to a carbon monoxide inlet line to one or more of the reactors in series, so as to adjust the total pressure over the plurality of reactors to the target pressure; and wherein the vent flow rate is detected by a detection means located in a vent line from one or more of the reactors in series, and a signal is transmitted to a carbon monoxide inlet line to one or more of the reactors in series, so as to adjust the vent flow rate over the plurality of reactors to the target vent flow rate.

17. The process of claim 1 wherein the carbon monoxide partial pressure is selected in the inverse order region of the hydroformylation rate curve corresponding to a hydroformylation reaction rate at the maximum or within 50 percent of the maximum rate, as determined from a plot of hydroformylation reaction rate versus carbon monoxide partial pressure.

18. A hydroformylation process comprising reacting in a reaction zone one or more olefinic unsaturated compounds with carbon monoxide and hydrogen in the presence of a metal-organopolyphosphite ligand complex catalyst and optionally a free organopolyphosphite ligand to produce a reaction product fluid comprising one or more aldehydes, and separating in at least one separation zone the one or more aldehydes from the metal-organopolyphosphite ligand complex catalyst and the optional free organopolyphosphite ligand, the improvement comprising:

conducting the hydroformylation process at a carbon monoxide partial pressure such that reaction rate increases as carbon monoxide partial pressure decreases and reaction rate decreases as carbon monoxide partial pressure increases; and wherein the following process steps are conducted to float the carbon monoxide partial pressure so as to stabilize reaction rate, total pressure, vent flow rate, reaction temperature, or a combination thereof; the process steps comprising at least one of the following process control schemes selected from:

Scheme A:
(a1) establishing a target total pressure;
(a2) detecting the total pressure, and determining the difference between the detected total pressure and the target total pressure; and
(a3) based on the pressure difference measured in step (a2), manipulating a feed flow of gas comprising carbon monoxide to adjust the detected total pressure essentially to the target total pressure;

Scheme B:
(b1) establishing a target vent flow rate;
(b2) detecting the vent flow rate, and determining the difference between the detected vent flow rate and the target flow rate; and
(b3) based on the vent flow rate difference measured in step (b2), manipulating a feed flow of gas comprising carbon monoxide to adjust the detected vent flow rate essentially to the target vent flow rate.

19. The process of claim 18 wherein process steps (a1) through (a3) and process steps (b1) through (b3) are all implemented so as to adjust the detected total pressure essentially to the target total pressure and to adjust the detected vent flow rate essentially to the target vent flow rate.

20. The process of claim 18 wherein the olefin comprises from 3 to about 20 carbon atoms.

21. The process of claim 18 wherein the metal of the metal-organopolyphosphite complex catalyst is rhodium.

22. The process of claim 18 wherein the carbon monoxide partial pressure ranges from about 1 psia (6.8 kPa) to about 1,000 psia (6,800 kPa).

23. An apparatus for stabilizing a hydroformylation process comprising:

a reactor comprising a means for feeding one or more reactants; a means for feeding a synthesis gas; optionally, a means for feeding a secondary source of carbon monoxide; a means for feeding a catalyst solution; a means for venting reaction and inert gases; a means for withdrawing a reaction fluid; a means for measuring total gas pressure; and a means for measuring vent flow rate of reaction and inert gases; the apparatus further comprising at least one of the following design schemes selected from:

Design A:
(a1) a means for determining a pressure differential between a target total gas pressure and the measured total gas pressure;
(a2) a means for generating a signal corresponding to the pressure differential;
(a3) a means for receiving the signal from (a2) and for determining and sending an output signal to manipulate the flow rate of synthesis gas and/or secondary source of carbon monoxide to adjust the measured total pressure to the target total pressure;

Design B:
(b1) a means for determining a vent flow rate differential between a target vent flow rate and the measured vent flow rate;
(b2) a means for generating a signal corresponding to the vent flow rate differential;
(b3) a means for receiving the signal from (b2) and for determining and sending an output signal to manipulate the flow rate of synthesis gas and/or secondary source of carbon monoxide to adjust the measured vent flow rate to the target vent flow rate.

24. The apparatus of claim 23 comprising all of design features (a1) through (a3) and design features (b1) through (b3).

25. The process of claim 1 wherein the hydroformylation process is conducted at a temperature greater than 50° C. and less than 120° C.

26. The process of claim 1 wherein the hydroformylation catalyst comprises rhodium metal and an organopolyphosphite ligand, such that the rhodium metal is employed in a concentration from 10 to 500 parts per million metal, calculated as free metal in the hydroformylation reaction fluid.

27. The process of claim 1 wherein the hydroformylation catalyst comprises a metal and an organopolyphosphite ligand, such that the ligand is employed in from 1.1 to 4 moles ligand per mole of metal present in the reaction fluid, said amount of ligand being the sum of both free ligand and ligand complexed to the metal in the reaction fluid.

28. The process of claim 1 wherein the partial pressure of carbon monoxide ranges from 15 psia (103.4 kPa) to 100 psia (689 kPa).

* * * * *